(12) United States Patent
Huelskamp

(10) Patent No.: US 12,004,937 B1
(45) Date of Patent: Jun. 11, 2024

(54) BLUNT DISSECTOR, DELIVERY AND DEPLOYMENT DEVICE FOR DELIVERY AND DEPLOYMENT OF SURGICAL MESH DURING SOFT TISSUE REPAIRS

(71) Applicant: Sheridan Technologies LLC, Fort Lauderdale, FL (US)

(72) Inventor: John W. Huelskamp, Barrington, IL (US)

(73) Assignee: Sheridan Technologies LLC, Fort Lauderdale, FL (US)

( * ) Notice: Subject to any disclaimer, the term of this patent is extended or adjusted under 35 U.S.C. 154(b) by 0 days.

(21) Appl. No.: 18/413,313

(22) Filed: Jan. 16, 2024

Related U.S. Application Data

(60) Provisional application No. 63/438,901, filed on Jan. 13, 2023.

(51) Int. Cl.
*A61F 2/00* (2006.01)

(52) U.S. Cl.
CPC .... *A61F 2/0063* (2013.01); *A61F 2002/0072* (2013.01)

(58) Field of Classification Search
CPC .................. A61F 2/0063; A61F 2002/0072
See application file for complete search history.

(56) References Cited

U.S. PATENT DOCUMENTS

| 751,415 | A | 2/1904 | Prindle |
|---|---|---|---|
| 2,330,693 | A | 9/1943 | Erdely |
| 4,333,471 | A | 6/1982 | KuNakaigel |
| 5,264,218 | A | 11/1993 | Rogozinski |
| 5,634,931 | A | 6/1997 | Kugel |
| 5,769,864 | A | 6/1998 | Kugel |
| D399,965 | S | 10/1998 | Laughlin et al. |
| D403,774 | S | 1/1999 | Laughlin et al. |

(Continued)

FOREIGN PATENT DOCUMENTS

| CA | 2201439 | 7/2004 |
|---|---|---|
| EP | 0783270 | 6/2004 |

(Continued)

OTHER PUBLICATIONS

Brauman, D., Diastasis Recti: Clinical Anatomy, Plastic and Reconstructive Surgery, Nov. 2008, vol. 122, No. 5, pp. 1564-1569.

(Continued)

*Primary Examiner* — Mohamed G Gabr
(74) *Attorney, Agent, or Firm* — Pandiscio & Pandiscio

(57) ABSTRACT

Apparatus for delivering a surgical mesh, the apparatus comprising: a hollow outer tube having a distal end and a proximal end; a distal housing mounted to the distal end of the hollow outer tube; a hollow inner tube having a distal end and a proximal end, wherein the hollow inner tube is slidably disposed within the hollow outer tube; a central rod having a distal end and a proximal end, wherein the central rod is slidably disposed within the hollow inner tube; an actuation element mounted to the proximal end of the central rod; and a surgical mesh carriage comprising a plurality of legs, wherein each of the plurality of legs comprises a first hinged end mounted to the distal end of the hollow inner tube and a second hinged end mounted to the distal end of the central rod.

19 Claims, 32 Drawing Sheets

(56) References Cited

U.S. PATENT DOCUMENTS

| | | | |
|---|---|---|---|
| 5,916,225 A | 6/1999 | Kugel | |
| D416,327 S | 11/1999 | Kugel | |
| 6,171,318 B1 | 1/2001 | Kugel et al. | |
| 6,174,320 B1 | 1/2001 | Kugel et al. | |
| 6,176,863 B1 | 1/2001 | Kugel et al. | |
| 6,224,616 B1 | 5/2001 | Kugel | |
| D445,188 S | 7/2001 | Walter | |
| 6,280,453 B1 | 8/2001 | Kugel et al. | |
| 6,290,708 B1 | 9/2001 | Kugel et al. | |
| 6,420,622 B1 | 7/2002 | Johnston et al. | |
| 6,544,167 B2 | 4/2003 | Buckberg et al. | |
| 6,669,735 B1 | 12/2003 | Pelissier | |
| 6,790,213 B2 | 9/2004 | Cherok et al. | |
| 6,800,082 B2 | 10/2004 | Rousseau | |
| 6,884,212 B2 | 4/2005 | Thierfelder et al. | |
| 7,396,975 B2 | 7/2008 | Sigurjonsson et al. | |
| 7,806,905 B2 | 10/2010 | Ford et al. | |
| 8,052,759 B2 * | 11/2011 | Dupic | A61F 2/0063 623/23.72 |
| 8,182,545 B2 | 5/2012 | Cherok et al. | |
| 8,562,633 B2 | 10/2013 | Cully et al. | |
| 9,072,586 B2 | 7/2015 | Ranucci et al. | |
| 9,308,068 B2 | 4/2016 | Spinnler et al. | |
| 9,820,837 B2 | 11/2017 | Cardinale et al. | |
| 9,980,802 B2 | 5/2018 | Bailly et al. | |
| 10,342,650 B2 | 7/2019 | Russo et al. | |
| 10,449,027 B2 | 10/2019 | Griffin et al. | |
| 11,857,403 B2 | 1/2024 | Huelskamp et al. | |
| 2002/0052649 A1 | 5/2002 | Greenhalgh | |
| 2003/0130745 A1 | 7/2003 | Cherok et al. | |
| 2003/0171823 A1 | 9/2003 | Zotti et al. | |
| 2003/0212460 A1 | 11/2003 | Darois et al. | |
| 2007/0276487 A1 | 11/2007 | Carteron et al. | |
| 2007/0299538 A1 | 12/2007 | Roeber | |
| 2008/0147099 A1 | 6/2008 | Uen | |
| 2011/0288567 A1 | 11/2011 | Ranucci et al. | |
| 2012/0232334 A1 | 9/2012 | Bell et al. | |
| 2013/0218125 A1 | 8/2013 | Stopek et al. | |
| 2013/0267970 A1 | 10/2013 | Cardinale et al. | |
| 2019/0099252 A1 | 4/2019 | Nelson et al. | |
| 2023/0210672 A1 | 7/2023 | Nie et al. | |

FOREIGN PATENT DOCUMENTS

| | | |
|---|---|---|
| EP | 2730297 | 5/2014 |
| WO | WO 2002/032346 | 4/2002 |
| WO | WO 2010/039249 | 4/2010 |

OTHER PUBLICATIONS

Chabert et al. Multicentre prospective feasibility study on the repair of hernias and incisional ventral hernias with an innovative Tintrap mesh, Journal of Visceral Surgery, Nov. 25, 2011, pp. e442-e446.

Ferzli et al., Chronic Pain after Inguinal Herniorrhaphy, J Am Coll Surg, 2007, vol. 205, No. 2, pp. 333-341.

Helgstrand et al., Trocar site hernia after laparoscopic surgery: a qualitative systematic review, Hernia, 2011, vol. 15, pp. 113-121.

Nahas et al., Rectus Diastasis Corrected with Absorbable Suture: A Long-Term Evaluation, Aesth Plast Surg, 2011, vol. 35, pp. 43-48.

Palanivelu et al., Laparoscopic repair of diastasis recti using the 'Venetian blinds' technique of plication with prosthetic reinforcement: a retrospective study, Hernia, 2009, vol. 13, pp. 287-292.

Sharma et al., Laparoscopic ventral/incisional hernia repair: a single centre experience of 1,242 patients over a period of 13 years, Hernia, 2011, vol. 15, pp. 131-139.

Snyder et al., Patient satisfaction, chronic pain, and quality of life after elective incisional hernia repair: effects of recurrence and repair technique, Hernia, 2011, vol. 15, pp. 123-129.

Wassenaar et al., Mesh-fixation method and pain and quality of life after laparoscopic ventral or incisional hernia repair: a randomized trial of three fixation techniques, Surg Endosc, 2009, vol. 24, pp. 1296-1302.

* cited by examiner

BLUNT DISSECTOR, DELIVERY AND DEPLOYMENT DEVICE FOR DELIVERY AND DEPLOYMENT OF SURGICAL MESH DURING SOFT TISSUE REPAIRS

REFERENCE TO PENDING PRIOR PATENT APPLICATION

This patent application claims benefit of prior U.S. Provisional Patent Application Ser. No. 63/438,901, filed Jan. 13, 2023 by Grant Technologies LLC and John W. Huelskamp for NOVEL BLUNT DISSECTOR, DELIVERY AND DEPLOYMENT DEVICE FOR DELIVERY AND DEPLOYMENT OF SURGICAL MESH DURING MINIMALLY-INVASIVE SURGICAL PROCEDURES.

The above-identified patent application is hereby incorporated herein by reference.

FIELD OF THE INVENTION

This invention relates to medical procedures and apparatus in general, and more particularly to medical procedures and apparatus for repairing soft tissue defects such as abdominal and inguinal hernias and the like.

BACKGROUND OF THE INVENTION

In the reconstruction of soft tissue defects in humans and animals, such as in abdominal and inguinal hernia repairs, surgical mesh is often used to reinforce the soft tissue defect so as to facilitate healing and to prevent subsequent defect recurrence. More particularly, when performing a closure of a soft tissue defect in an anatomical wall (e.g., to repair an abdominal hernia), it is common to secure a surgical mesh to the soft tissue at the edge of the soft tissue defect, with some overlap between the surgical mesh and the soft tissue, so as to increase the healed strength of the surgical repair. The surgical mesh is typically secured to the soft tissue adjacent to the soft tissue defect with suture or tacks.

In practice, and looking now at FIGS. 1-3, in open procedures the soft tissue reconstruction is typically carried out using a "skirted" surgical mesh 5. Skirted surgical mesh 5 generally comprises a base layer 10 of surgical mesh terminating in an outer edge 12, and a continuous "skirt" or rim 15 of surgical mesh terminating in an outer edge 17 and an inner edge 18 which defines a central opening 19. Continuous skirt or rim 15 overlies the outer portion of base layer 10 (e.g., so that outer edge 17 of continuous skirt or rim 15 is substantially aligned with outer edge 12 of base layer 10), and continuous skirt or rim 15 is secured to base layer 10 only at or adjacent to outer edge 17 of continuous skirt or rim 15, such that the inner portions of continuous skirt or rim 15 (i.e., the portions adjacent to inner edge 18) can be lifted away from base layer 10 when desired. As a result, continuous skirt or rim 15 provides an easily accessed section of surgical mesh which facilitates fixation of skirted surgical mesh 5 to the soft tissue, i.e., by fixing continuous skirt or rim 15 of skirted surgical mesh 5 to the edges of the soft tissue defect using conventional suture or tack fixation. By providing skirted surgical mesh 5 with the continuous skirt or rim 15 of mesh material, when skirted surgical mesh 5 is being secured to the soft tissue, the sharp ends of the fixation elements (e.g., the suture needle or tack) are isolated from the delicate internal organs of the patient by base layer 10, whereby to prevent inadvertent damage to the delicate internal organs of the patient.

However, it has been found that when pulling up on continuous skirt or rim 15 of skirted surgical mesh 5 (e.g., for suturing and/or tacking), this pulling up of the continuous skirt or rim 15 can cause base layer 10 to distort significantly (e.g., to transform from a smooth planar configuration to a curved configuration, such as is shown in FIG. 4). Such distortion in base layer 10 of skirted surgical mesh 5 can make it difficult to provide a flat, symmetrical repair which is smooth and comfortable for the patient. More particularly, the configurations of surgical mesh used in these types of soft tissue repairs (e.g., the hernia meshes used in abdominal hernia repairs) are normally circular or oval in shape (FIGS. 2-4 show exemplary surgical meshes which are oval in shape) and can possess very tight radii, particularly at the longitudinal ends 25 of oval skirted surgical meshes 5 (see FIGS. 2 and 4). As the radii of continuous skirt or rim 15 of skirted surgical mesh 5 becomes tighter, the effect of "pulling up" on the continuous skirt or rim 15 of skirted surgical mesh 5 (e.g., with graspers 30, FIG. 4) is increasingly distorting to base layer 10 of skirted surgical mesh 5.

Efforts have been made to reduce this distortion of base layer 10 of skirted surgical mesh 5 when pulling up on continuous skirt or rim 15 of skirted surgical mesh 5.

In one such effort, and looking now at FIG. 5, the inner edge 18 of continuous skirt or rim 15 is scalloped (i.e., a portion of inner edge 18 of continuous skirt or rim 15 is recessed, such as is shown in FIG. 5 at 40, from the remainder of inner edge 18 in an effort to minimize the distortion of base layer 10 of skirted surgical mesh 5 when pulling up on continuous skirt or rim 15 of skirted surgical mesh 5. Unfortunately, in practice, this approach has proven to be of limited benefit.

In another such effort, and looking now at FIG. 6, a surgical mesh 45 is provided which comprises a base layer 50 of surgical mesh which is completely covered with a top layer 55 of surgical mesh, with top layer 55 being secured to base layer 50 about the outer edge (s) 60 of the two layers, and with top layer 55 being bifurcated at 65 so as to provide two separate pockets of surgical mesh. Then, during use, a first half of top layer 55 of surgical mesh 45 is pulled upward for fixation (e.g., by gripping the first half of top layer 55 with graspers 30 at the bifurcation line 65) and then the second half of the top layer 55 of surgical mesh 45 is pulled upward for fixation (e.g., by gripping that second half of top layer 55 with graspers 30 at bifurcation line 65). Unfortunately, this construction still suffers from distortion of base layer 50 when one or both halves of top layer 55 of surgical mesh 45 is drawn upward for fixation.

Thus there is a need for a surgical mesh which provides a skirt or rim of surgical mesh about the outer perimeter of a base layer of surgical mesh but which allows the skirt or rim of surgical mesh to be manipulated without distorting the smooth planar configuration of the base layer of surgical mesh.

In addition to the foregoing, it will be appreciated that open surgical intervention in the region of the human abdomen or groin or other soft tissue targets (e.g., to effect a hernia repair) can result in an extended period of convalescence for the patient. Thus there is also a need for a device that facilitates fast and simple delivery and deployment of surgical mesh during soft tissue repairs including open, minimally invasive and robotic procedures.

SUMMARY OF THE INVENTION

The present invention comprises the provision and use of a surgical mesh which provides a skirt or rim of surgical mesh about the outer perimeter of a base layer of surgical mesh.

The present invention also comprises the provision and use of a device for delivery and deployment of surgical mesh.

In one preferred form of the invention, there is provided a segmented skirted surgical mesh for use in reconstructing a soft tissue defect, the segmented skirted surgical mesh comprising:
- a base layer of surgical mesh, said base layer of surgical mesh comprising an outer edge; and
- a segmented continuous skirt of surgical mesh comprising an outer edge and an inner edge which defines a central opening, said segmented continuous skirt of surgical mesh being secured to said base layer of surgical mesh at said outer edge of said segmented continuous skirt of surgical mesh, and said segmented continuous skirt of surgical mesh comprising a plurality of slits formed in said segmented continuous skirt of surgical mesh, wherein said plurality of slits extend outwardly from said inner edge of said segmented continuous skirt of surgical mesh, whereby to form a plurality of flaps of surgical mesh in said segmented continuous skirt of surgical mesh, such that at least one of said flaps of surgical mesh can be lifted away from said base layer of surgical mesh and secured to soft tissue without causing distortion of said base layer of surgical mesh.

In another preferred form of the invention, there is provided a method for reconstructing a soft tissue defect, the method comprising:
- providing a segmented skirted surgical mesh comprising:
  - a base layer of surgical mesh, said base layer of surgical mesh comprising an outer edge; and
  - a segmented continuous skirt of surgical mesh comprising an outer edge and an inner edge which defines a central opening, said segmented continuous skirt of surgical mesh being secured to said base layer of surgical mesh at said outer edge of said segmented continuous skirt of surgical mesh, and said segmented continuous skirt of surgical mesh comprising a plurality of slits formed in said segmented continuous skirt of surgical mesh, wherein said plurality of slits extend outwardly from said inner edge of said segmented continuous skirt of surgical mesh, whereby to form a plurality of flaps of surgical mesh in said segmented continuous skirt of surgical mesh, such that at least one of said flaps of surgical mesh can be lifted away from said base layer of surgical mesh and secured to soft tissue without causing distortion of said base layer of surgical mesh;
- positioning said segmented skirted surgical mesh adjacent to a soft tissue defect; and
- lifting at least one of said flaps of surgical mesh away from said base layer of surgical mesh and securing said at least one flap of surgical mesh to soft tissue without causing distortion of said base layer of surgical mesh.

In yet another preferred form of the present invention, there is provided a device for delivery and deployment of surgical mesh.

In one preferred form of the invention, there is provided apparatus for delivering a surgical mesh, the apparatus comprising:
- a hollow outer tube having a distal end and a proximal end;
- a distal housing mounted to the distal end of the hollow outer tube;
- a hollow inner tube having a distal end and a proximal end, wherein the hollow inner tube is slidably disposed within the hollow outer tube;
- a central rod having a distal end and a proximal end, wherein the central rod is slidably disposed within the hollow inner tube;
- an actuation element mounted to the proximal end of the central rod; and
- a surgical mesh carriage comprising a plurality of legs, wherein each of the plurality of legs comprises a first hinged end mounted to the distal end of the hollow inner tube and a second hinged end mounted to the distal end of the central rod.

In another preferred form of the invention, there is provided a method for delivering a surgical mesh, the method comprising:
- providing apparatus for delivering a surgical mesh, the apparatus comprising:
  - a hollow outer tube having a distal end and a proximal end;
  - a distal housing mounted to the distal end of the hollow outer tube;
  - a hollow inner tube having a distal end and a proximal end, wherein the hollow inner tube is slidably disposed within the hollow outer tube;
  - a central rod having a distal end and a proximal end, wherein the central rod is slidably disposed within the hollow inner tube;
  - an actuation element mounted to the proximal end of the central rod; and
  - a surgical mesh carriage comprising a plurality of legs, wherein each of the plurality of legs comprises a first hinged end mounted to the distal end of the hollow inner tube and a second hinged end mounted to the distal end of the central rod;
- advancing the apparatus through an incision to a surgical site;
- moving the actuation element distally to a first location, whereby to project the surgical mesh carriage out of the distal housing;
- moving the actuation element distally to a second location, whereby to hinge each of the plurality of legs at their respective first hinged ends and cause the plurality of legs to assume a radially-expanded configuration; and
- delivering a surgical mesh to the surgical site.

In another preferred form of the invention, there is provided apparatus for delivering a surgical mesh, the apparatus comprising:
- a hollow outer tube having a distal end and a proximal end;
- a distal housing mounted to the distal end of the hollow outer tube;
- a hollow inner tube slidably disposed within the hollow outer tube having a distal end and a proximal end, wherein the proximal end of the hollow inner tube comprises a locking collar;
- a central rod having a distal end and a proximal end, wherein the central rod is slidably disposed within the hollow inner tube;
- an actuation element mounted to the proximal end of the central rod;
- a surgical mesh carriage comprising a plurality of legs, wherein each of the plurality of legs comprises a first hinged end mounted to the distal end of the hollow inner tube and a second hinged end mounted to the distal end of the central rod; and a handle comprising a locking tab mounted to the proximal end of the hollow outer tube;

wherein the apparatus is configured such that when (i) the actuation element is moved distally to a first location, the central rod and the hollow inner tube move distally so as to move the surgical mesh carriage out of the distal housing, and (ii) the actuation element is moved distally to a second location the central rod moves distally and hinges each of the plurality of legs at their respective first hinged ends so as to assume a radially-expanded configuration; and wherein distal movement of the actuation element to the second location causes the locking collar to audibly snap over the locking tab so as to provide feedback to a user indicating that the plurality of legs are in the radially-expanded configuration.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
FIG. 1 is a schematic view showing a soft tissue defect being reconstructed using a surgical mesh.
Figure 2:
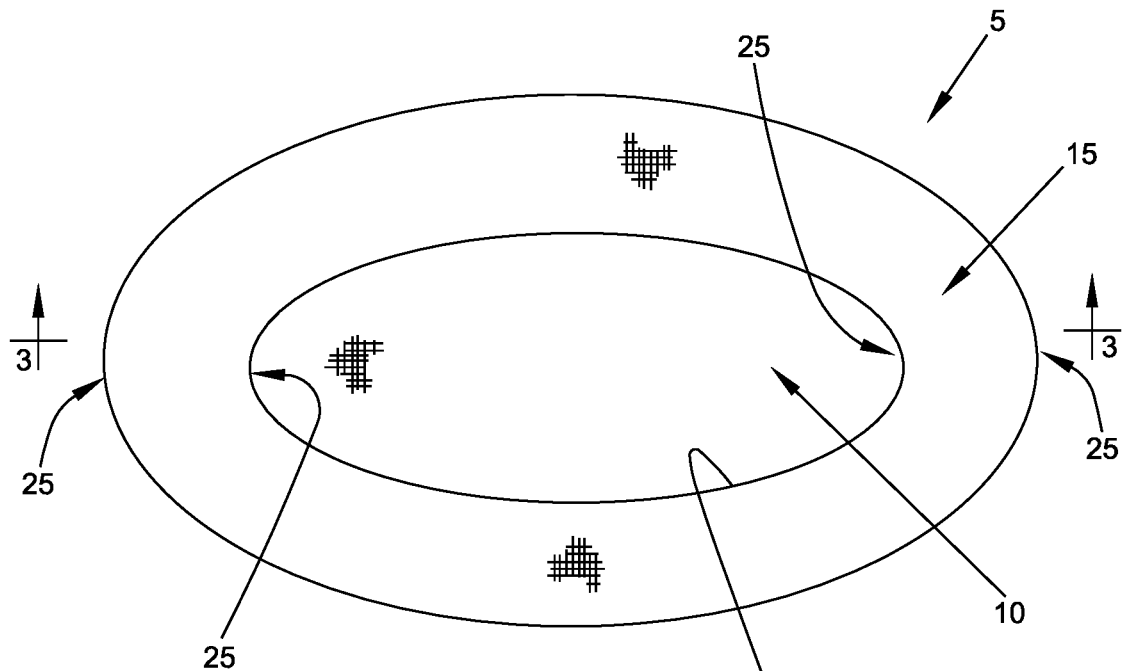
FIGS. 2 and 3 are schematic views showing a prior art skirted surgical mesh in greater detail.
Figure 3:
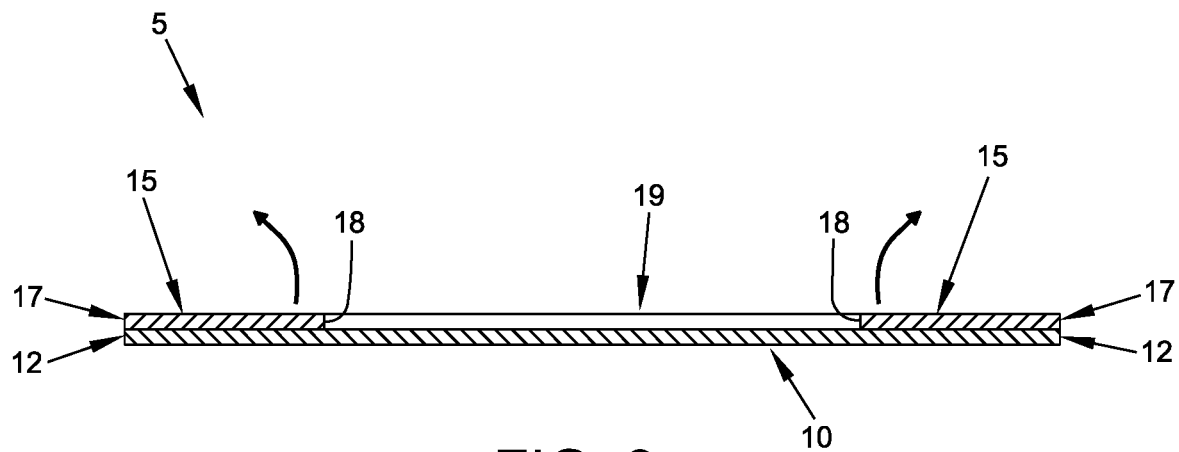
Figure 4:
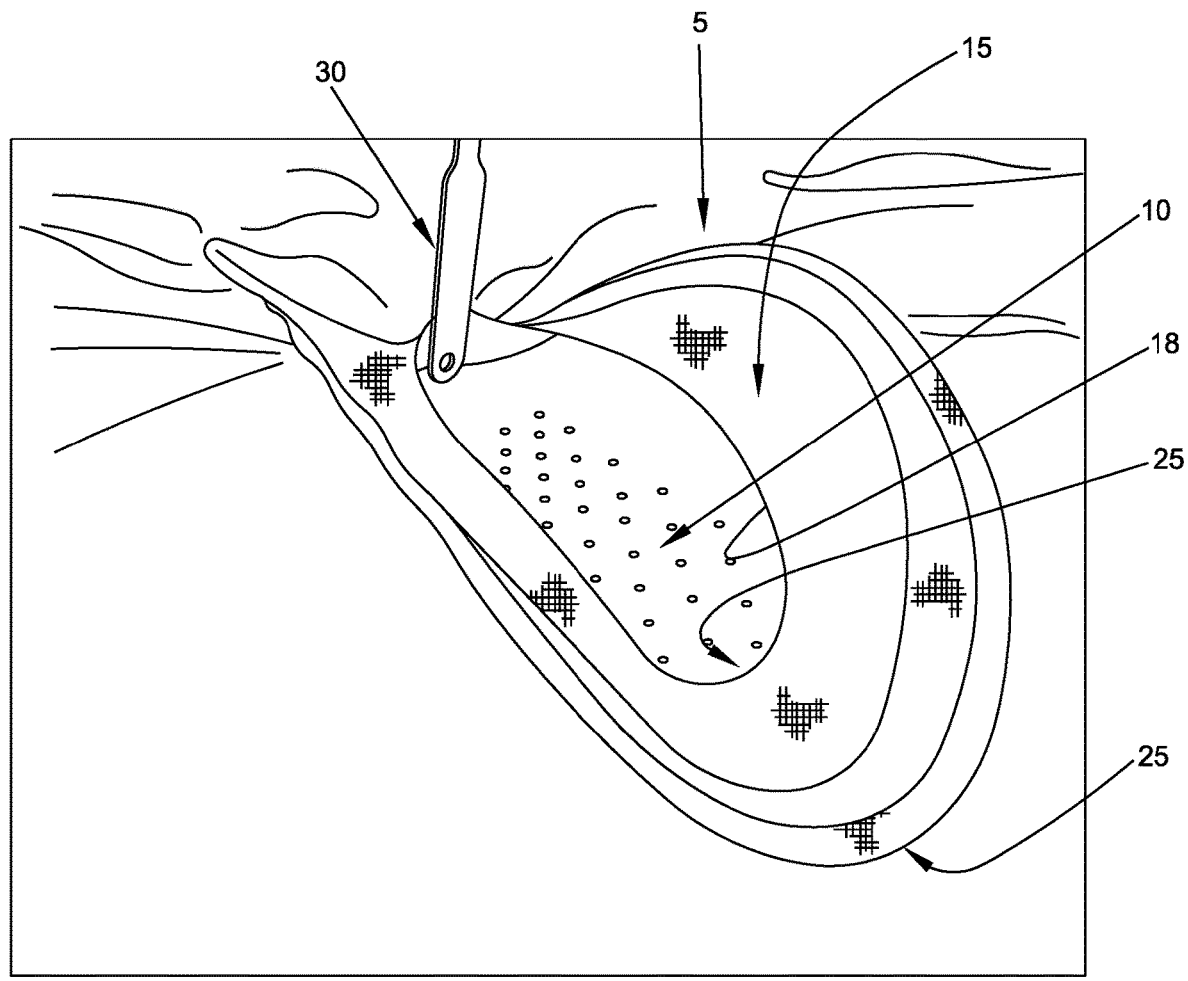
FIG. 4 is a schematic view showing the prior art skirted surgical mesh of FIGS. 2 and 3 becoming distorted as the continuous skirt or rim of the skirted surgical mesh is lifted away from the base layer of the skirted surgical mesh.
Figure 5:
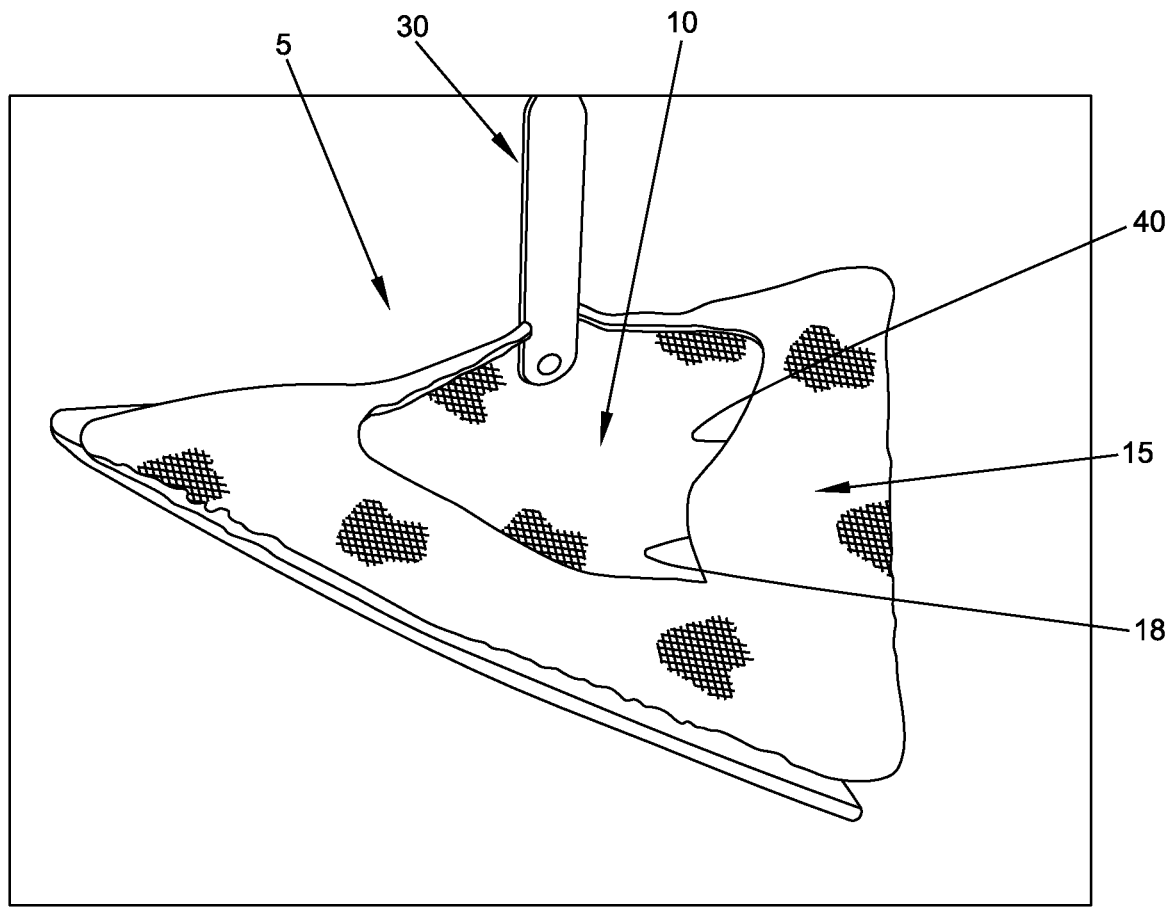
FIG. 5 is a schematic view showing a prior art skirted surgical mesh wherein the inner edge of the continuous skirt or rim of the surgical mesh is scalloped in an effort to minimize distortion of the base layer of the skirted surgical mesh as the continuous skirt or rim of the skirted surgical mesh is lifted away from the base layer of the skirted surgical mesh.
Figure 6:
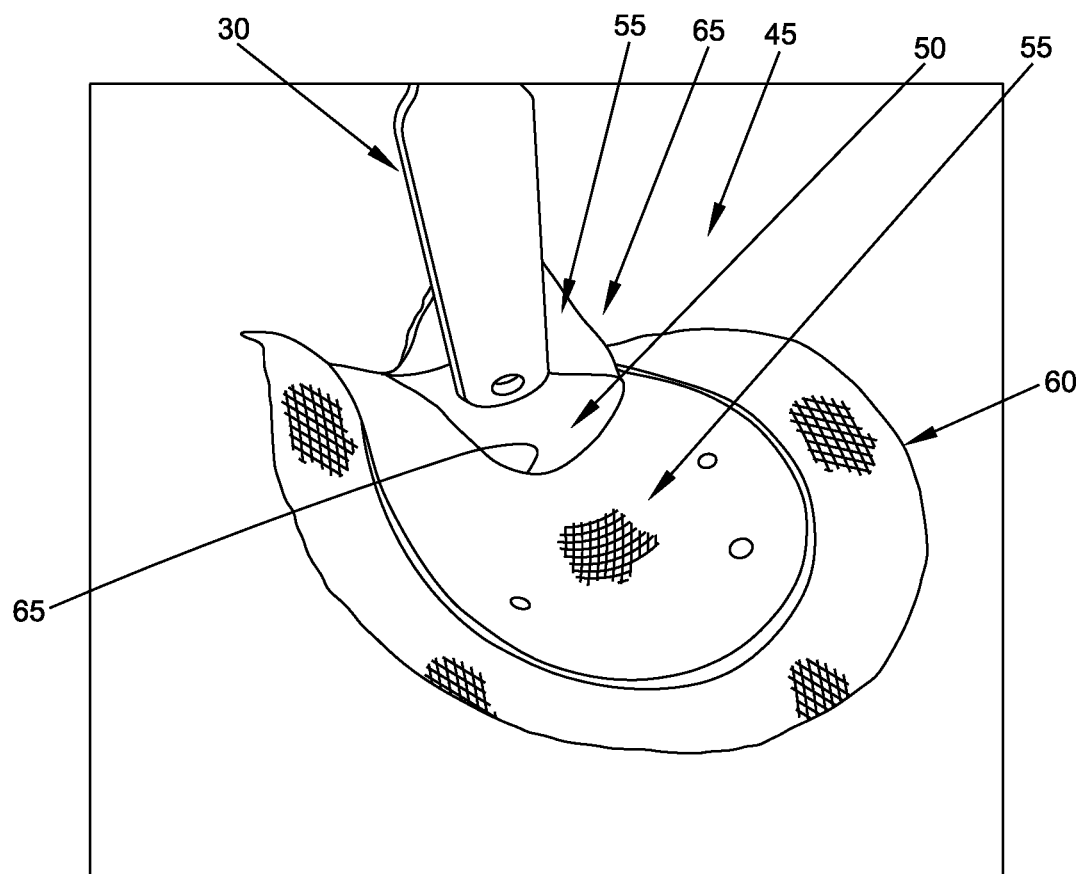
FIG. 6 is a schematic view showing a prior art surgical mesh which comprises a base layer of surgical mesh which is completely covered with a top layer of surgical mesh, with the top layer of surgical mesh being secured to the base layer of surgical mesh about the outer edges of the two layers, and with the top layer of surgical mesh being bifurcated so as to provide two separate pockets of surgical mesh.
Figure 7:
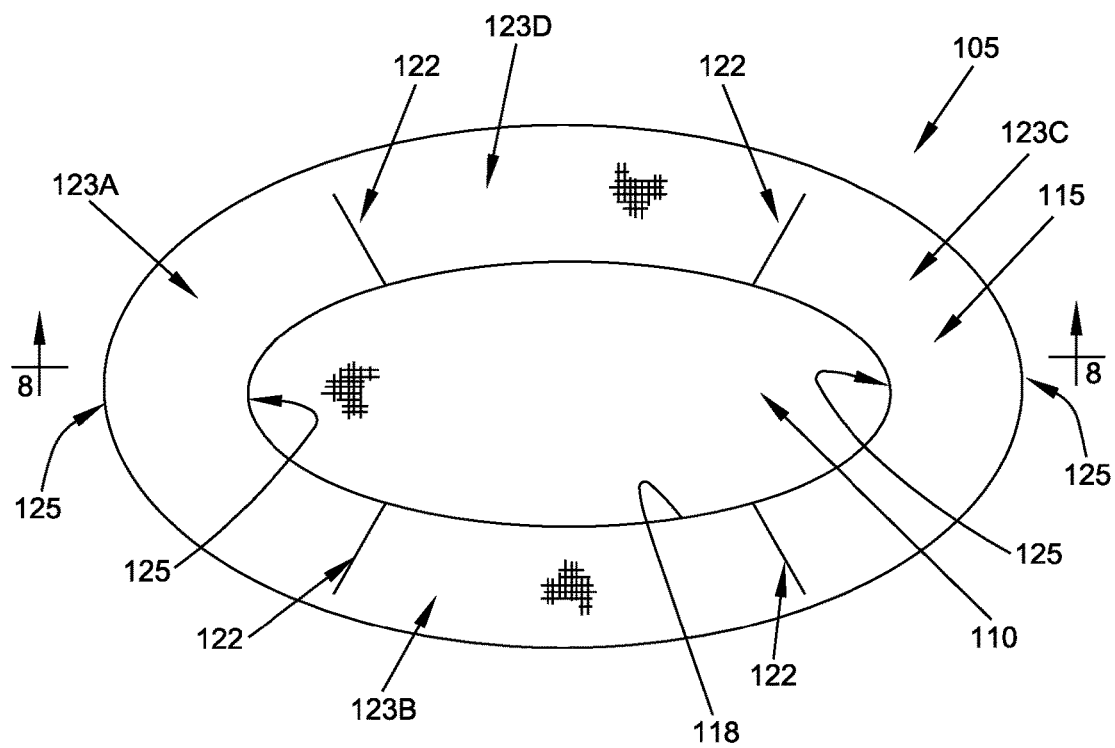
FIGS. 7-10 are schematic views showing a segmented skirted surgical mesh formed in accordance with the present invention.
Figure 8:
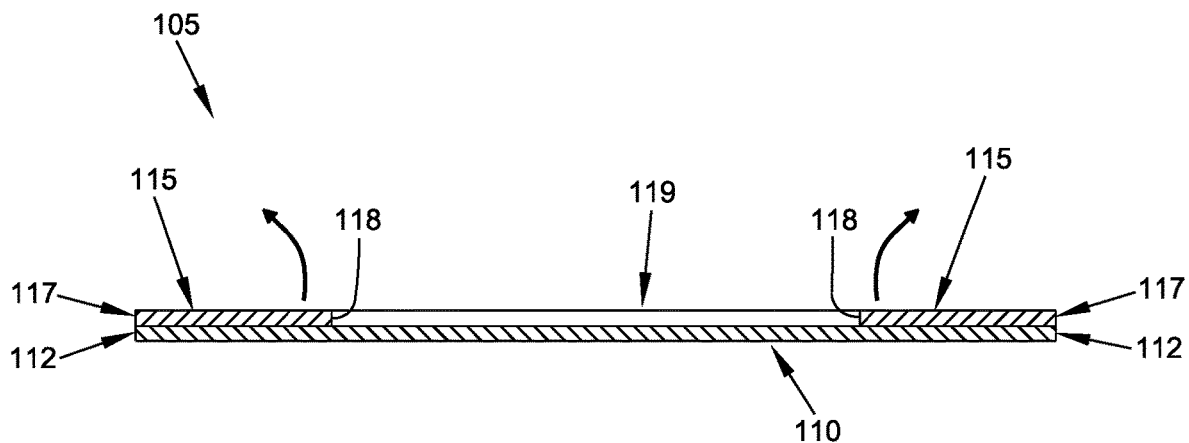
Figure 9:
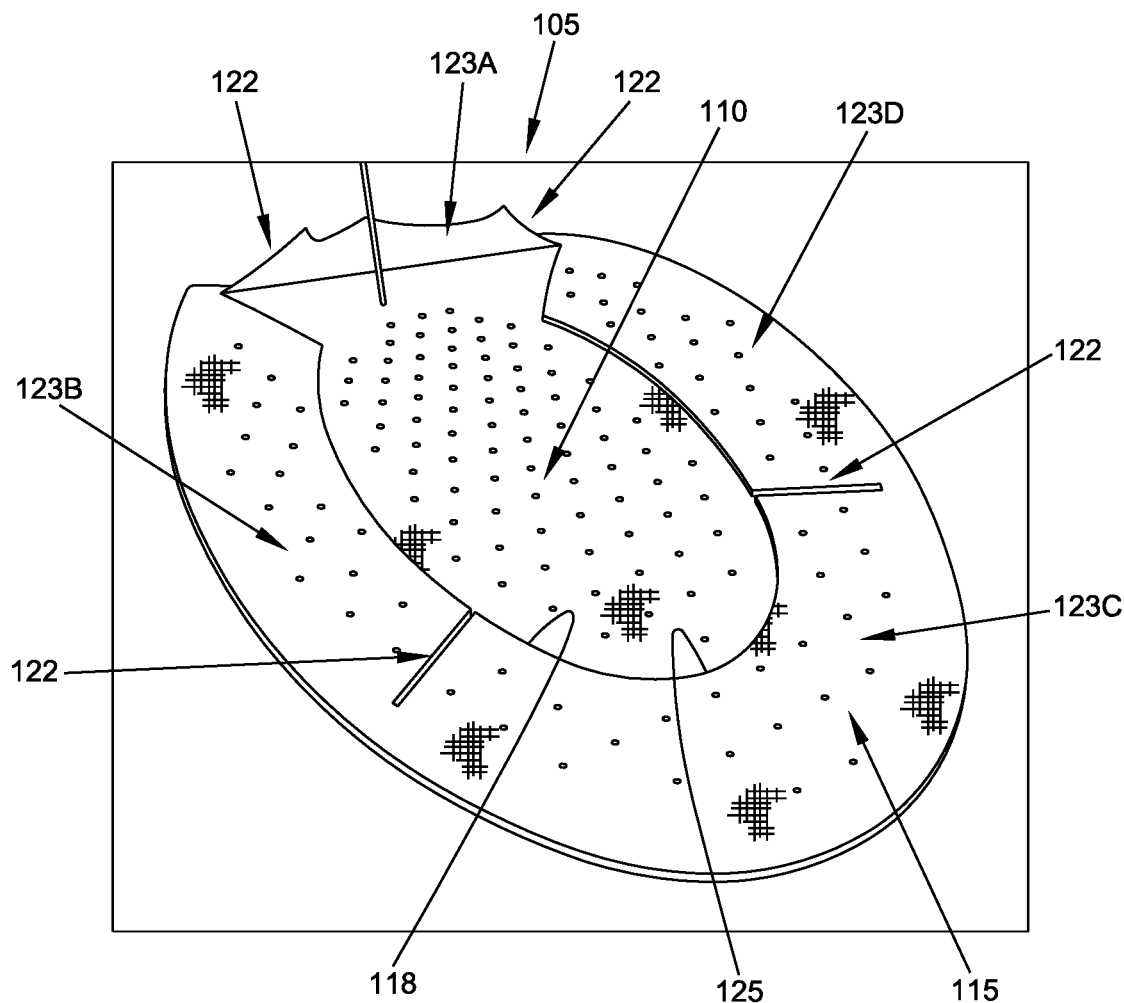
Figure 10:
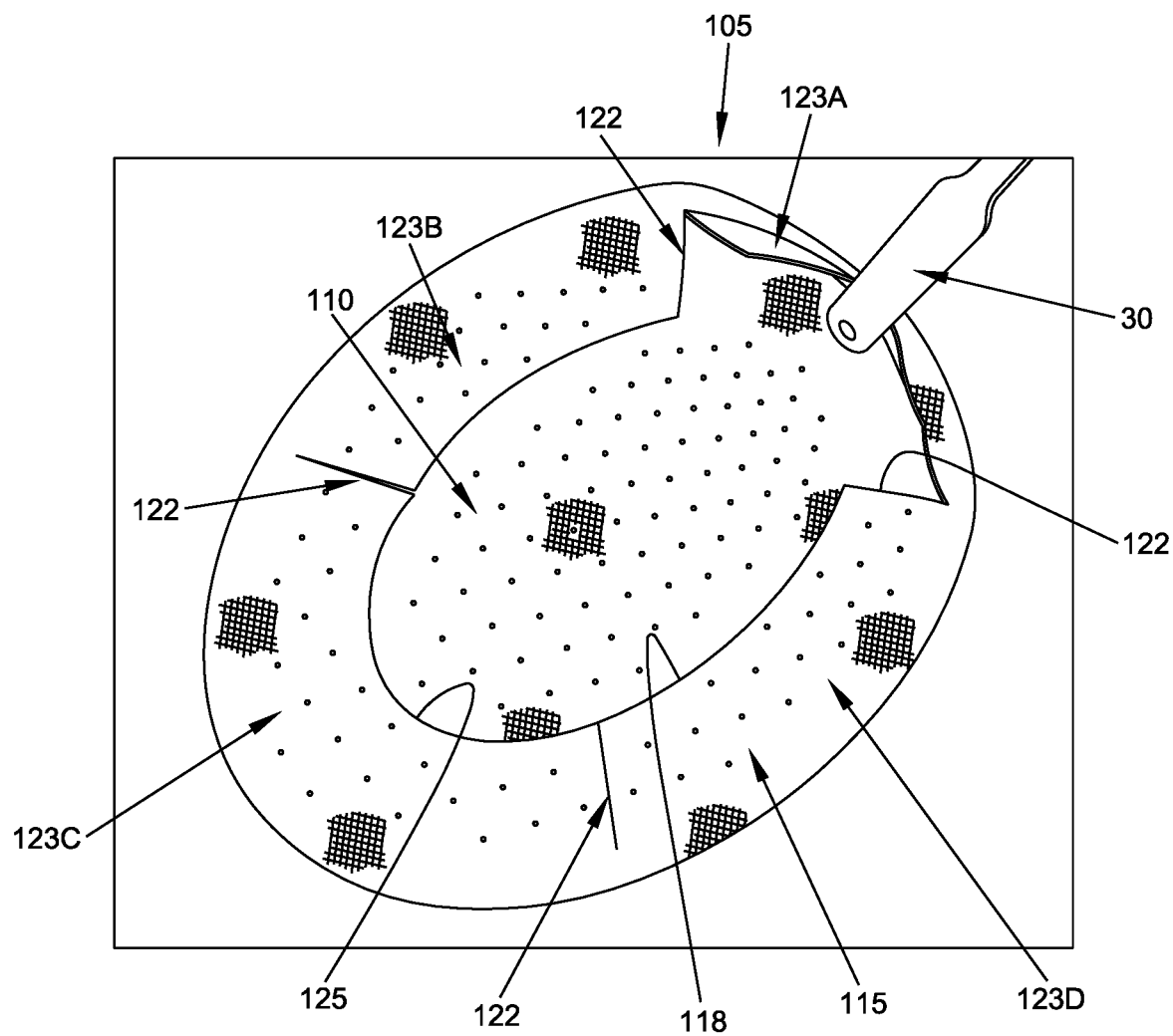

The present invention comprises the provision and use of a surgical mesh which provides a skirt or rim of surgical mesh about the outer perimeter of a base layer of surgical mesh.

The present invention also comprises the provision and use of a blunt dissector, delivery and deployment device to facilitate the delivery and deployment of surgical mesh during soft tissue repairs including open, minimally invasive and robotic procedures.

Segmented Skirted Surgical Mesh 105

Looking now at FIGS. 7-10, the present invention comprises the provision and use of a segmented skirted surgical mesh 105. Segmented skirted surgical mesh 105 comprises a base layer 110 of surgical mesh terminating in an outer edge 112, and a segmented continuous skirt or rim 115 of surgical mesh terminating in an outer edge 117 and an inner edge 118 which defines a central opening 119. Segmented continuous skirt or rim 115 overlies the outer portion of base layer 110 (e.g., so that outer edge 117 of segmented continuous skirt or rim 115 is substantially aligned with outer edge 112 of base layer 110), and segmented continuous skirt or rim 115 is secured to base layer 110 only at or adjacent to outer edge 117 of segmented continuous skirt or rim 115, such that the inner portions of segmented continuous skirt or rim 115 (i.e., the portions adjacent to inner edge 118) can be lifted away from base layer 110 when desired.

The segmented continuous skirt or rim 115 of surgical mesh is segmented by providing a plurality of breaks or cuts or slits 122 in the continuity of segmented continuous skirt or rim 115 of surgical mesh 105, whereby to form a plurality of segments or flaps 123A, 123B, 123C, etc. of the segmented continuous skirt or rim 115. In one preferred form of the invention, there are at least three breaks or cuts or slits 122 in the continuity of segmented continuous skirt or rim 115 of surgical mesh 105, whereby to form at least three segments or flaps 123A, 123B, 123C, etc.

Each of the segments or flaps 123A, 123B, 123C, etc. of segmented continuous skirt or rim 115 provides an easily accessed section of surgical mesh which facilitates fixation of segmented skirted surgical mesh 105 to the soft tissue, i.e., by fixing the various segments or flaps 123A, 123B, 123C, etc. of segmented continuous skirt or rim 115 to the edges of the soft tissue defect using conventional suture or tack fixation. By providing segmented skirted surgical mesh 5 with the segmented continuous skirt or rim 115 of surgical mesh, when segmented skirted surgical mesh 105 is being secured to the soft tissue, the sharp ends of the fixation elements (e.g., the suture needle or tack) are isolated from the delicate internal organs of the patient by base layer 110 of segmented skirted surgical mesh 105, whereby to prevent inadvertent damage to the delicate internal organs of the patient. At the same time, and significantly, by providing a segmented continuous skirt or rim 115 of surgical mesh, where the segmented continuous skirt or rim 115 is segmented (through the provision of breaks or cuts or slits 122) into a plurality of segments or flaps 123A, 123B, 123C, etc., distortion of base layer 110 of segmented skirted surgical mesh 105 can be reduced or eliminated when segmented continuous skirt or rim 115 is pulled upward, since then only the surgical mesh of a particular segment or flap 123A, 123B, 123C, etc. is pulled upward—the remainder of the segments or flaps 123A, 123B, 123C, etc. of the segmented continuous skirt or rim 115 are unaffected, which results in reduced distortion of base layer 110 of segmented skirted surgical mesh 105.

By way of example but not limitation, having three or four or more evenly-spaced breaks or cuts or slits 122 in segmented continuous skirt or rim 115 of a small oval or circular segmented skirted surgical mesh 105 keeps base layer 110 of segmented skirted surgical mesh 105 substantially flat even when some or all of segments or flaps 123A, 123B, 123C, etc. of the segmented continuous skirt or rim 115 is lifted up from base layer 110 of segmented skirted surgical mesh 105 (FIGS. 7-10), since then only the surgical mesh of a particular segment or flap 123A, 123B, 123C, etc. is pulled upward—the remainder of the segments or flaps 123A, 123B, 123C, etc. are unaffected, which results in reduced distortion of base layer 110 of segmented skirted surgical mesh 105.

In larger constructions, an oval configuration (FIGS. 7-10) is typically used, inasmuch as defects in a body wall cavity (e.g., an abdominal hernia) are typically oblong in shape (due to the stress orientation in the soft tissue). These oval configurations have opposing tight end radii 125 which benefit even more than circular configurations by providing breaks or cuts or slits 122 in segmented continuous skirt or rim 115.

Figure 11:
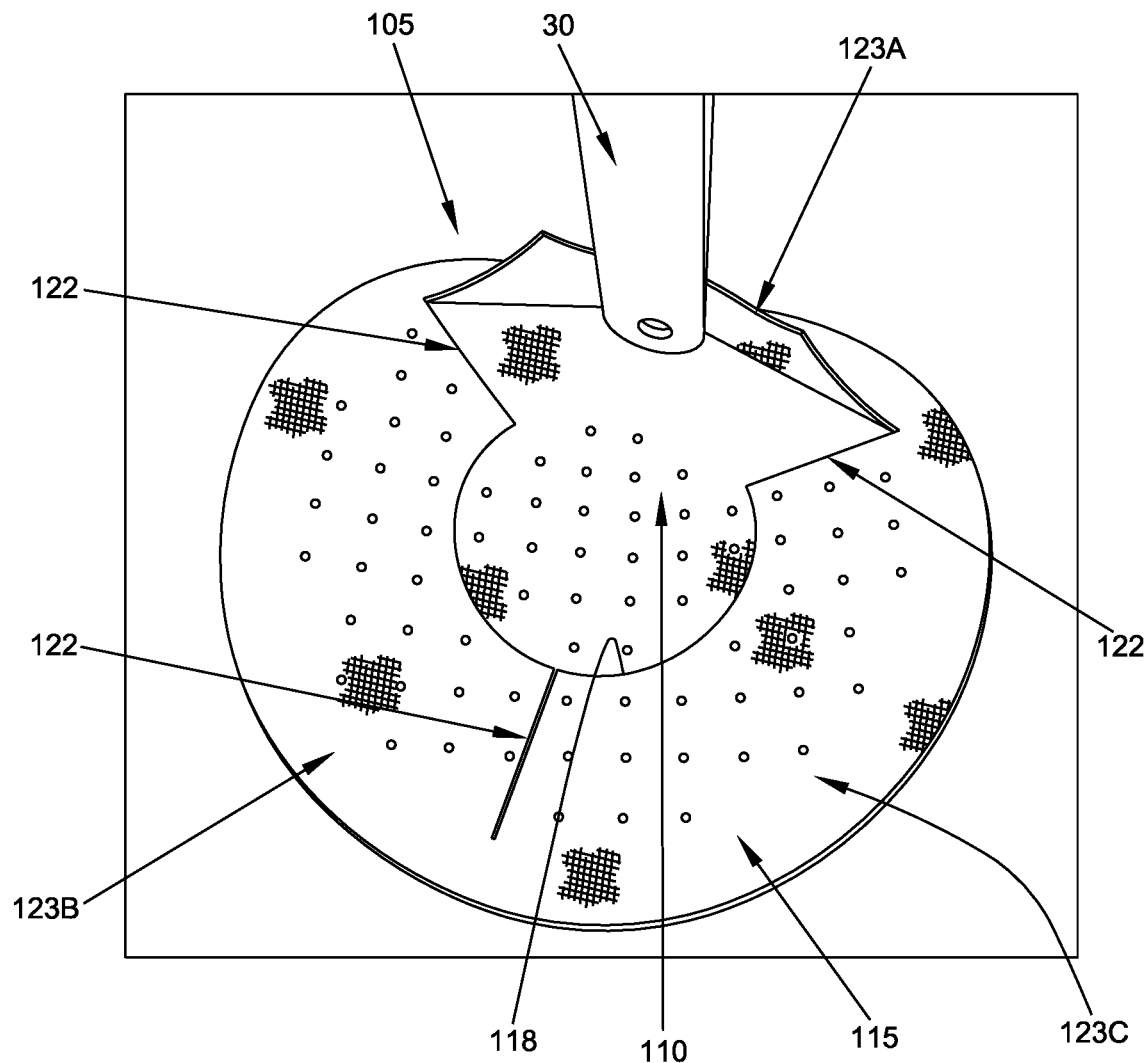
FIGS. 11 and 12 are schematic views showing another segmented skirted surgical mesh formed in accordance with the present invention.
Figure 12:
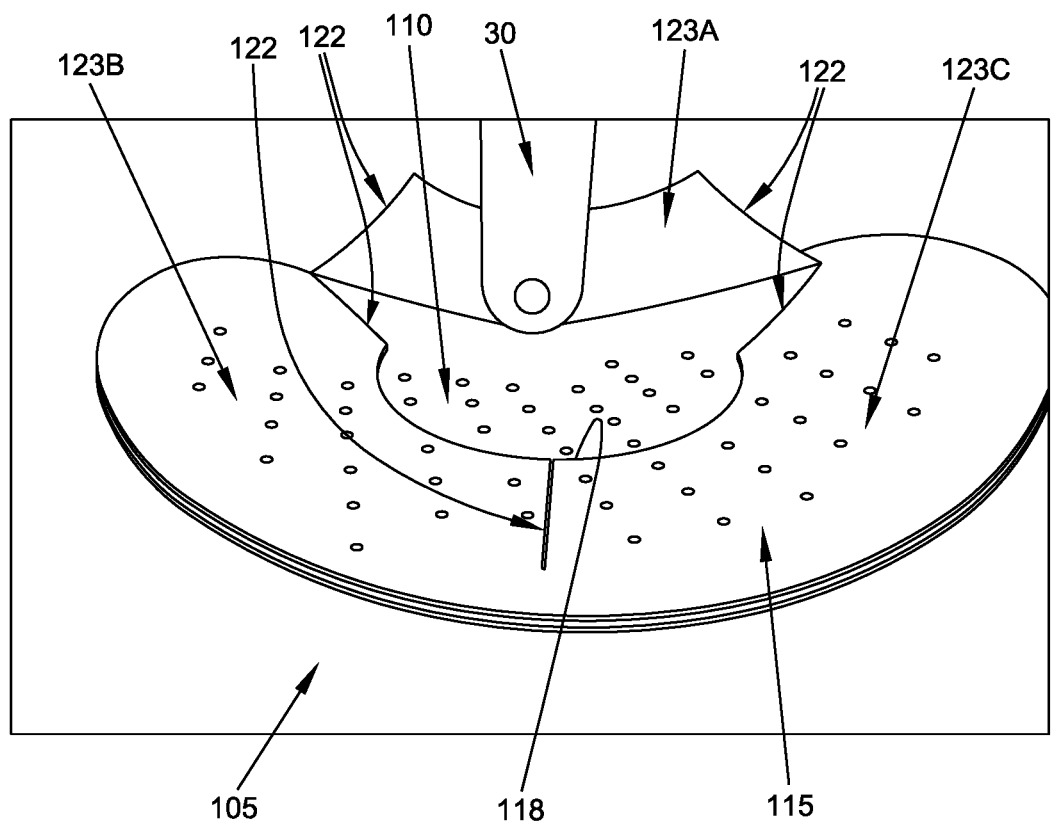

FIGS. 11 and 12 show a segmented skirted surgical mesh 105 having a circular configuration. Note that the segmented continuous skirt or rim 115 of segmented skirted surgical mesh 105 of FIGS. 11 and 12 has three breaks or cuts or slits 122, whereby to provide three segments or flaps 123A, 123B and 123C.

The breaks or cuts or slits 122 in segmented continuous skirt or rim 115 of segmented skirted surgical mesh 105 are preferably accomplished by cutting through segmented continuous skirt or rim 115, preferably starting at inner edge 118 of segmented continuous skirt or rim 115 and extending radially outwardly, and preferably terminating just short of the outer edge 117 of segmented continuous skirt or rim 115. In one preferred embodiment, breaks or cuts or slits 122 extend at an angle of 90 degrees to the adjacent inner edge 118 of segmented continuous skirt or rim 115. Alternatively, the breaks or cuts or slits 122 in segmented continuous skirt or rim 115 may be made at varying angles to inner edge 118 of segmented continuous skirt or rim 115 so as to further minimize distortion in base layer 110 of segmented skirted surgical mesh 105 when segments or flaps 123A, 123B, 123C, etc. are subjected to lifting away from base layer 110.

Figure 13:
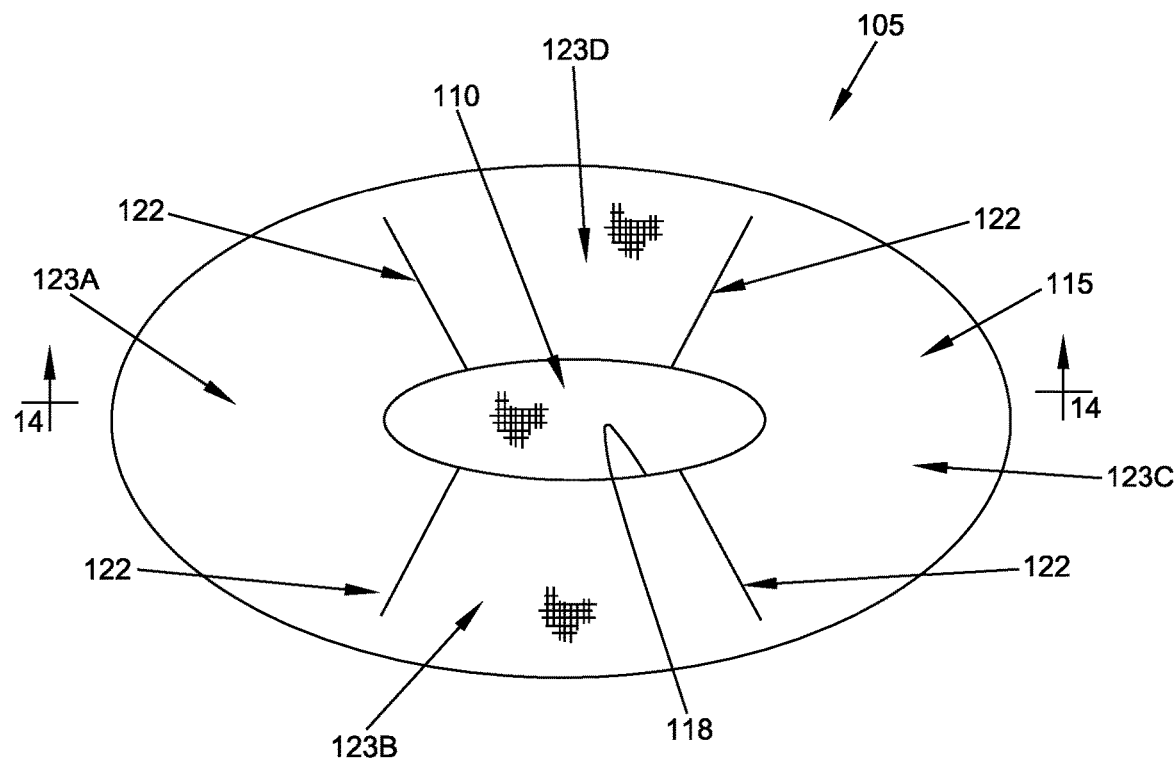
FIGS. 13-15 are schematic views showing another segmented skirted surgical mesh formed in accordance with the present invention.
Figure 14:
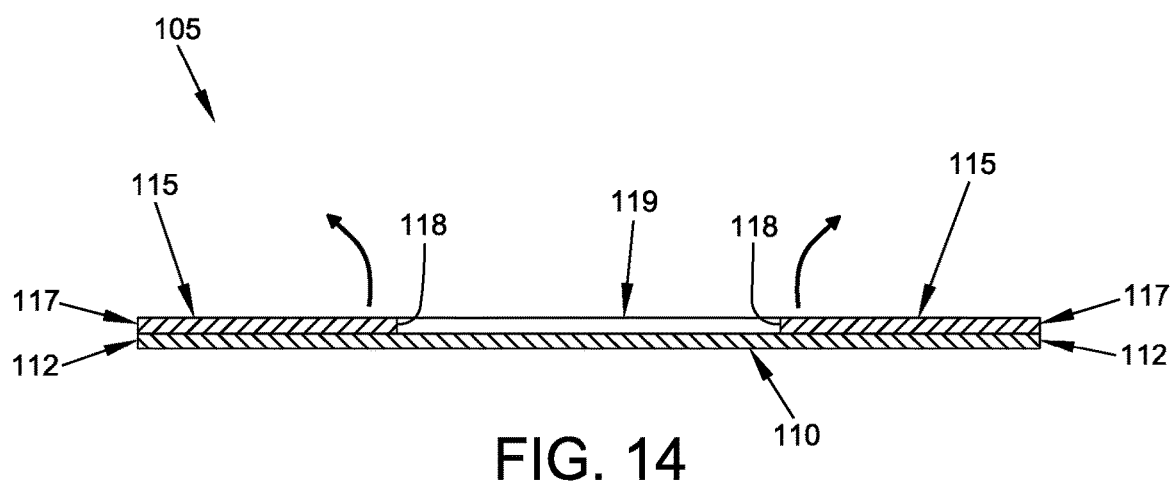
Figure 15:
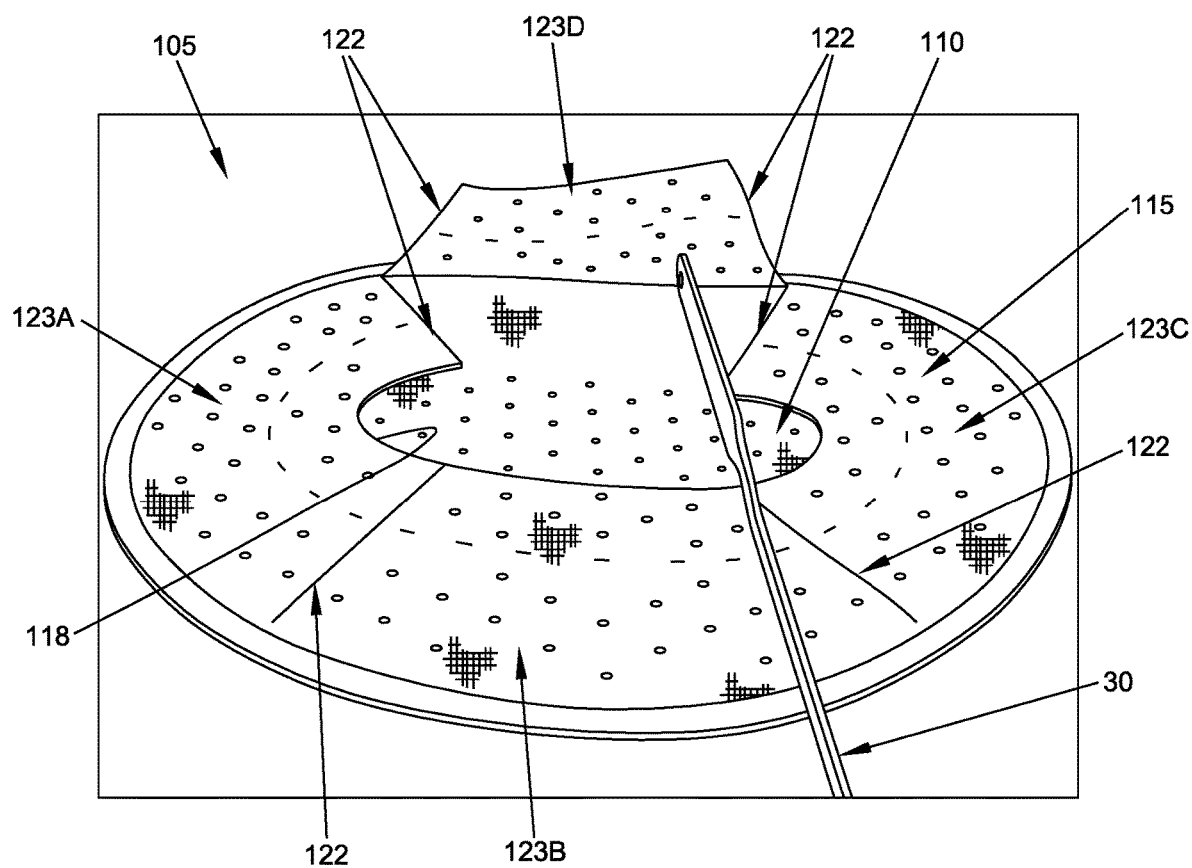
Figure 16:
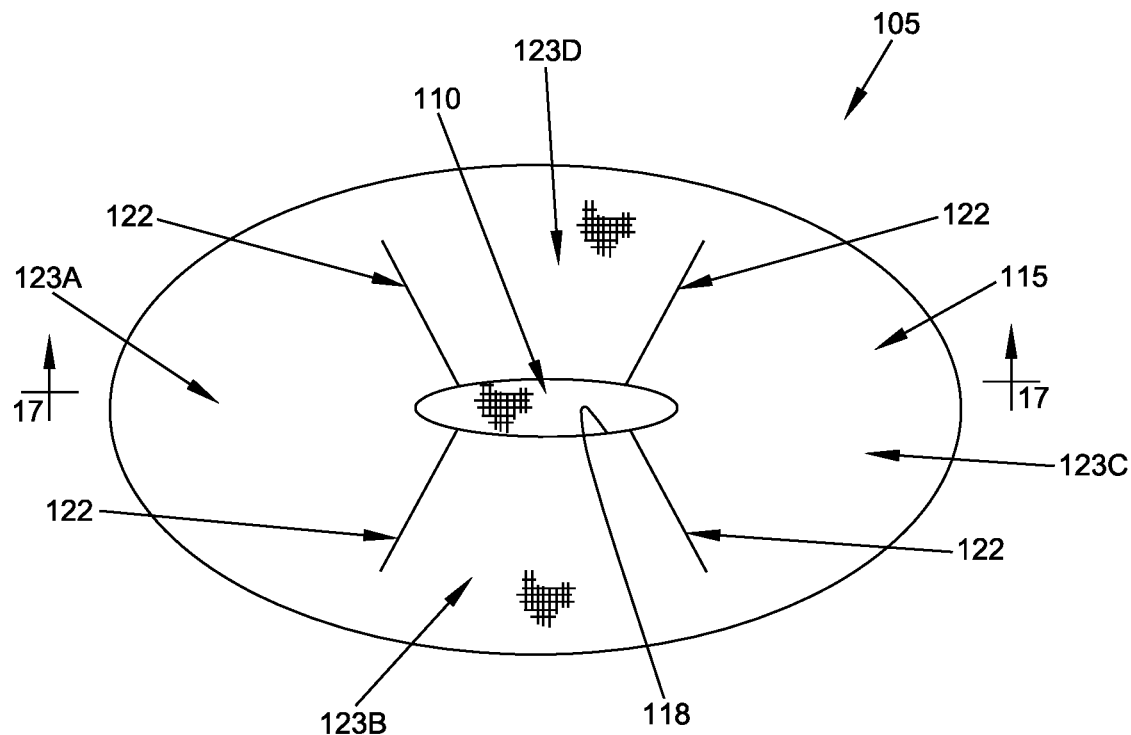
FIGS. 16-18 are schematic views showing another segmented skirted surgical mesh formed in accordance with the present invention.
Figure 17:
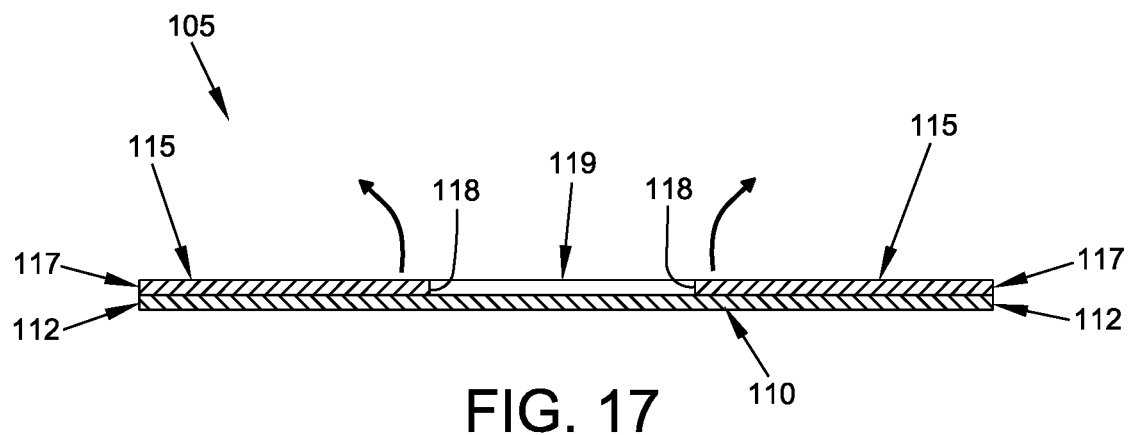
Figure 18:
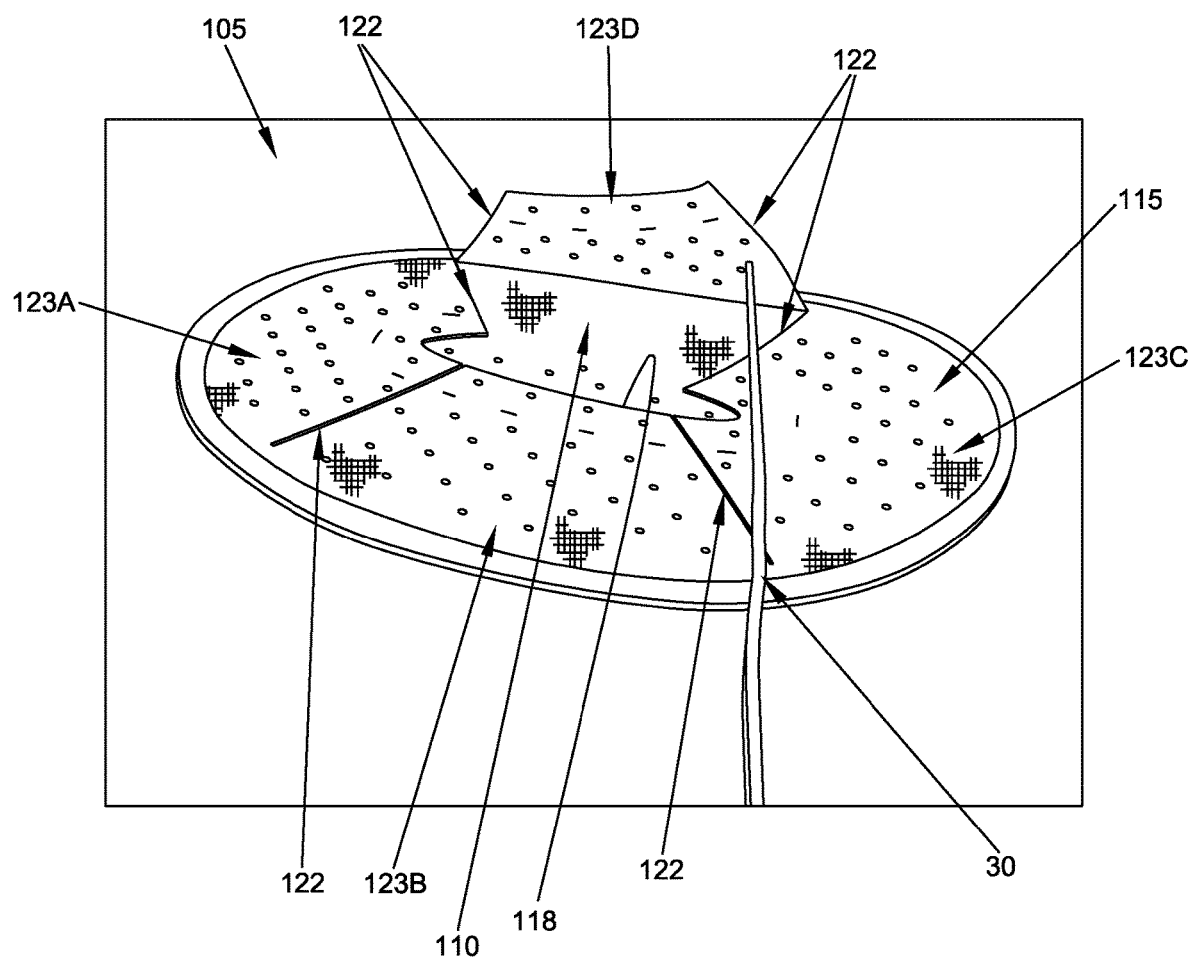

FIGS. 13-15 show another segmented skirted surgical mesh formed in accordance with the present invention. And FIGS. 16-18 show still another segmented skirted surgical mesh formed in accordance with the present invention. Note that with the segmented skirted surgical meshes of FIGS. 13-15 and FIGS. 16-18, segmented continuous skirt or rim 115 is modified so as to provide different sized central openings 119.

The breaks or cuts or slits 122 in segmented continuous skirt or rim 115 preferably extend almost all the way to outer edge 117 of segmented continuous skirt or rim 115, although the breaks or cuts or slits may also extend all the way to outer edge 117 if desired, or may terminate intermediate of segmented continuous skirt or rim 115 if desired.

The number of cuts or breaks or slits 122 formed in segmented continuous skirt or rim 115 of segmented skirted surgical mesh 105, and the placement of those breaks or cuts or slits 122, may be optimized so as to (i) minimize distortion of base layer 110 when a segment or flap 123A, 123B, 123C, etc. is pulled upward, and (ii) minimize the overall number of segments or flaps 123A, 123B, 123C, etc. that the segmented continuous skirt or rim 115 is divided into (since "too many segments or flaps" has the potential to complicate the fixation process for the surgeon). In practice, it is generally preferred to make three or four cuts or breaks or slits 122 in the segmented continuous skirt or rim 115 of segmented skirted surgical mesh 105, whereby to provide three or four segments or flaps 123A, 123B, 123C, etc. in segmented continuous skirt or rim 115 of segmented skirted surgical mesh 105, since providing less than three cuts or breaks or slits 122 in segmented continuous skirt or rim 115 makes it difficult to lift the segments or flaps of continuous segmented skirt or rim 115 away from base layer 110 without distorting base layer 110.

It should also be appreciated that, if desired, outer edge 117 of segmented continuous skirt or rim 115 could terminate inboard of outer edge 112 of base layer 110. Alternatively, outer edge 117 of segmented continuous skirt or rim 115 could overlap outer edge 112 of base layer 110 (e.g., outer edge 117 of segmented continuous skirt or rim 115 could be folded over edge 112 of base layer 110).

By minimizing the distortion of base layer 110 of segmented skirted surgical mesh 105 when one or more of the segments or flaps 123A, 123B, 123C, etc. of segmented continuous skirt or rim 115 is lifted up during fixation, the fixation itself is facilitated, i.e., the fixation will take less time and the final repair geometry is controlled so that there are no gathered areas that might lead to potential sites of discomfort for the patient. Thus, the segmented skirted surgical mesh of the present invention benefits both the surgeon (through facilitated fixation) and the patient (by producing a more cosmetic and comfortable reconstruction).

And, as will be discussed in further detail below, the segmented skirted surgical mesh allows for the use of a device that facilitates fast and simple delivery and deployment of the surgical mesh.

Blunt Dissector, Delivery and Deployment Device 205

As discussed above, there exists a need for a new and improved method and apparatus for quickly and easily delivering and deploying surgical mesh (e.g., the aforementioned segmented skirted surgical mesh 105 or other surgical mesh) to a surgical site in a minimally-invasive manner.

Figure 19:
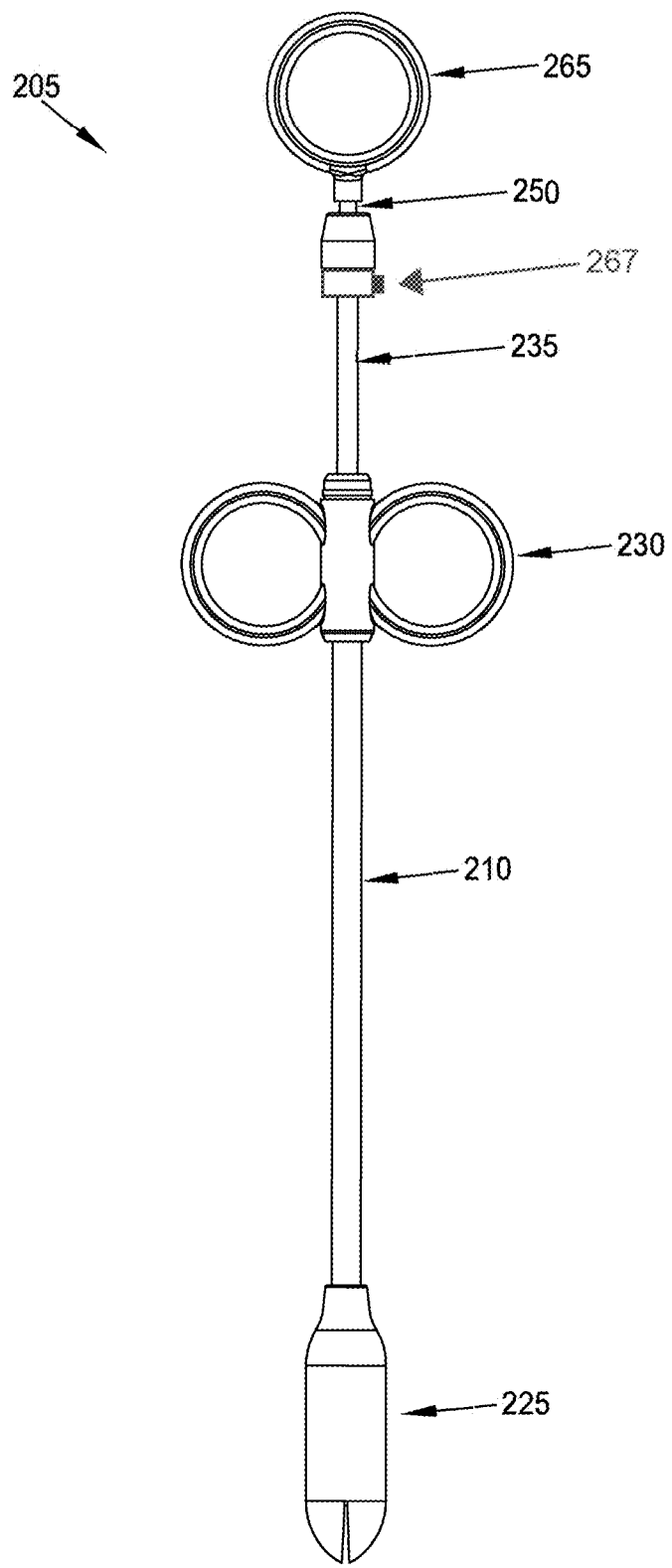
FIG. 19 is a schematic view showing a surgical mesh delivery device formed in accordance with the present invention.
Figure 20:
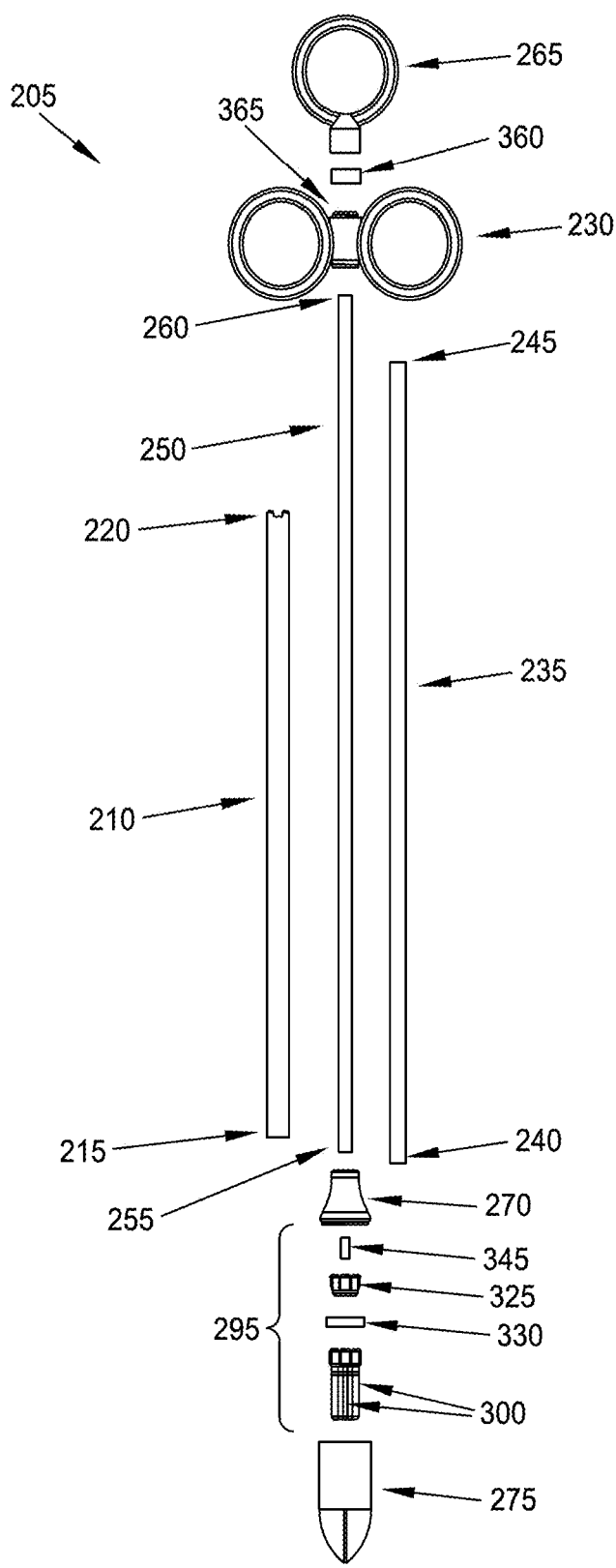
FIG. 20 is an exploded view of the surgical mesh delivery device of FIG. 19.

To that end, and looking now at FIGS. 19 and 20, there is shown a novel device 205 (also sometimes referred to herein as an all-in-one blunt dissector, delivery and deployment device or surgical mesh delivery device) formed in accordance with the present invention. Device 205 generally comprises a hollow outer tube 210 having a distal end 215 and a proximal end 220. A distal housing 225 is mounted to distal end 215 of hollow outer tube 210, and a handle 230 is mounted to proximal end 220 of hollow outer tube 210.

A hollow inner tube 235 having a distal end 240 and a proximal end 245 is slidably disposed within hollow outer tube 210 so as to be able to selectively move longitudinally relative thereto. A central rod (or tube) 250 comprising a distal end 255 and a proximal end 260 is slidably disposed within hollow inner tube 235 so as to be able to selectively move longitudinally relative thereto. An actuation element 265 is mounted to proximal end 260 of central rod 250, whereby to permit a user (e.g., a surgeon) to effect selective longitudinal movement of central rod 250 and/or hollow inner tube 235 by moving actuation element 265 distally or proximally, as will hereinafter be discussed in further detail.

Device 205 is configured such that (i) central rod 250 has a greater length than hollow inner tube 235 and hollow outer tube 210, and (ii) hollow inner tube 235 has a greater length than hollow outer tube 210.

In one preferred form of the present invention, a removable pre-deployment locking clip 267 is mounted to proximal end 245 of hollow inner tube 235 (see FIG. 19) so as to prevent movement of central rod 250. Removable pre-deployment locking clip 267 may comprise a release tab for gripping by a user. It will be appreciated that removable pre-deployment locking clip 267 functions in a manner that will be apparent to one of skill in the art in view of the present disclosure.

As a result of the foregoing construction, it will be appreciated that when actuation element 265 of central rod 250 is moved distally to a first location (after removal of pre-deployment locking clip 267), central rod 250 and hollow inner tube 235 move distally, and further distal movement of actuation element 265 to a second location causes further distal movement of only central rod 250 (i.e., hollow inner tube 235 moves distally with central rod 250 until hollow inner tube 235 reaches its distalmost location whereupon central rod 250 can continue to be moved until reaching its own distalmost location). Thus, in the foregoing construction, hollow outer tube 210 is fixed and remains stationary while central rod 250 is moved via actuation element 265, and hollow inner tube 235 moves with central rod 250 until hollow inner tube 235 reaches its distalmost location.

Figure 21:
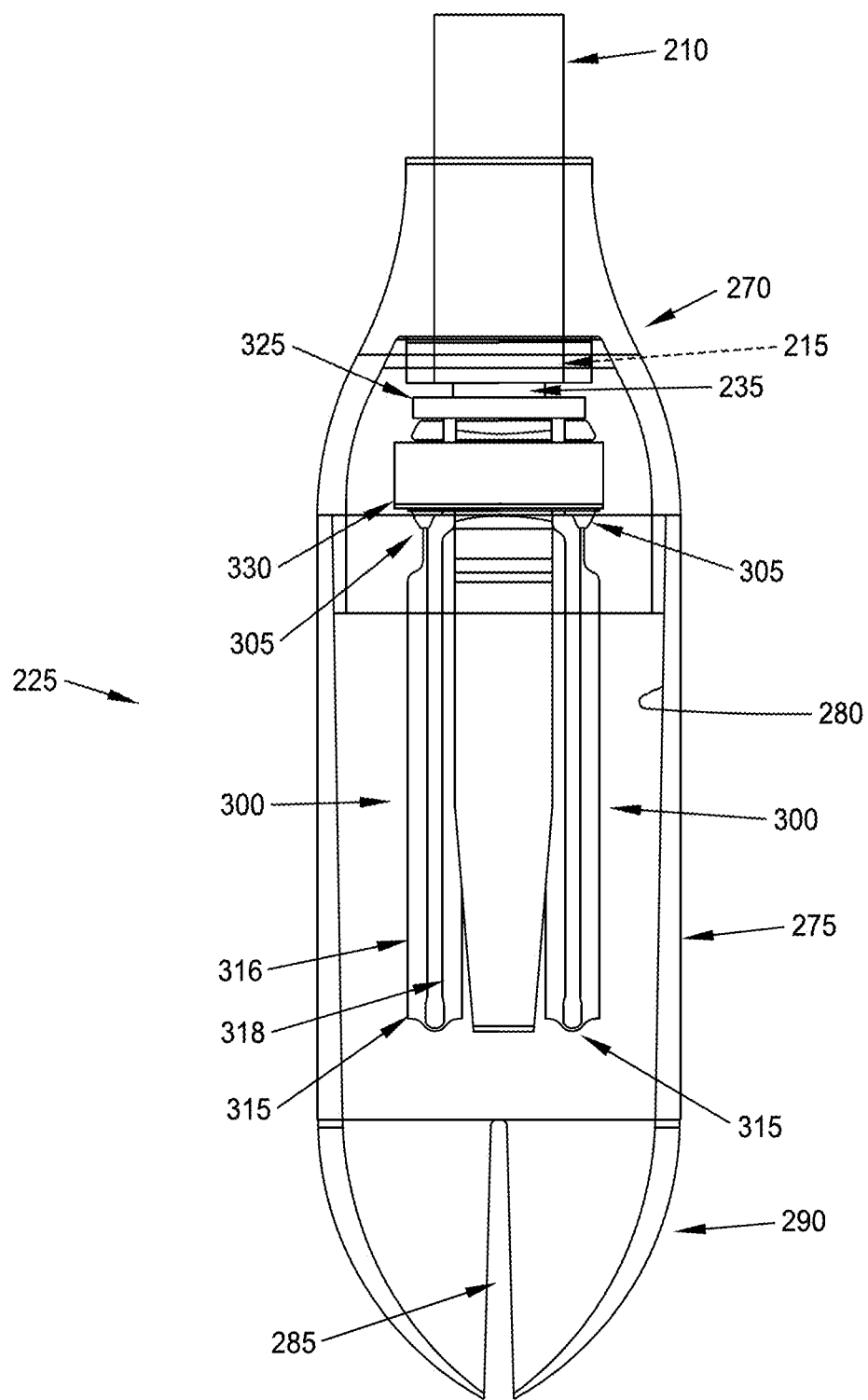
FIGS. 21-23 are schematic views showing further aspects of the surgical mesh delivery device of FIG. 19.
Figure 22:
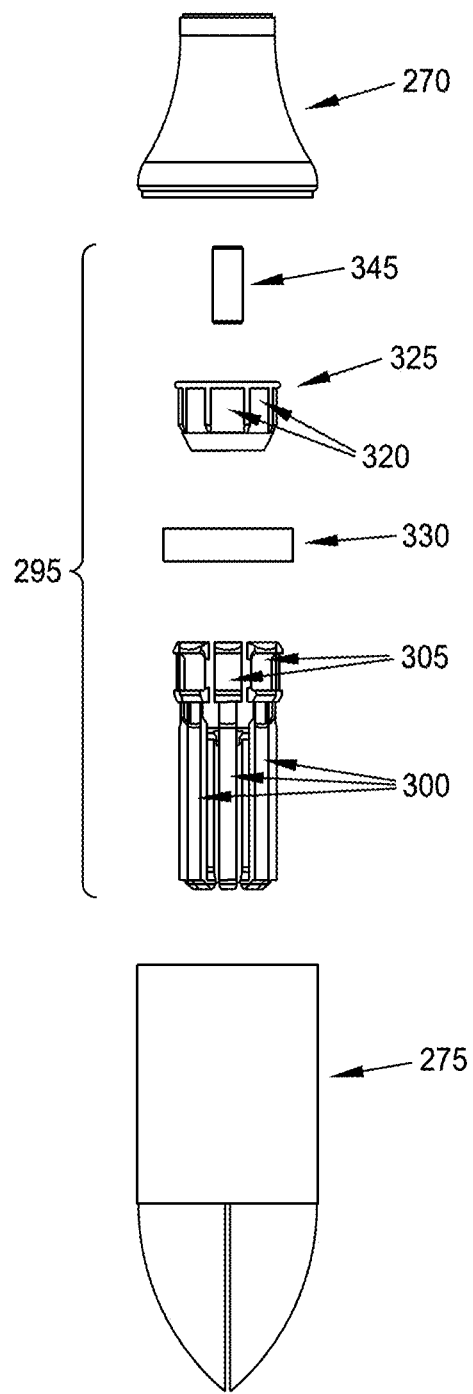
Figure 23:
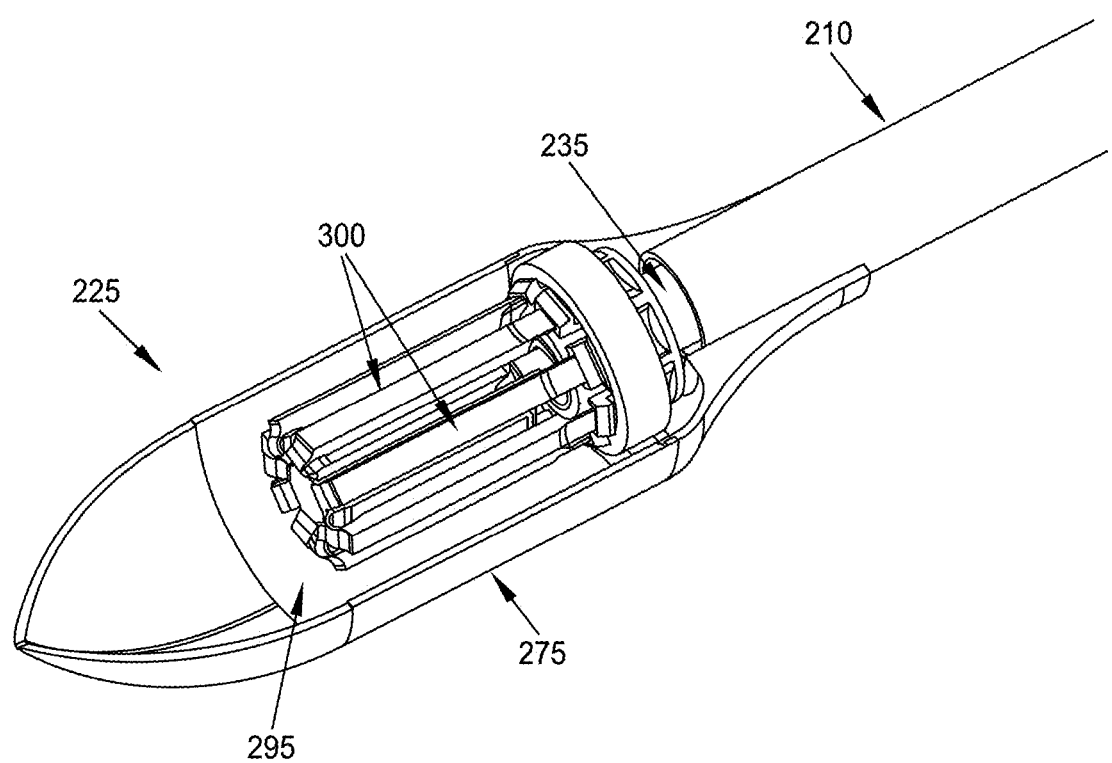
Figure 24:
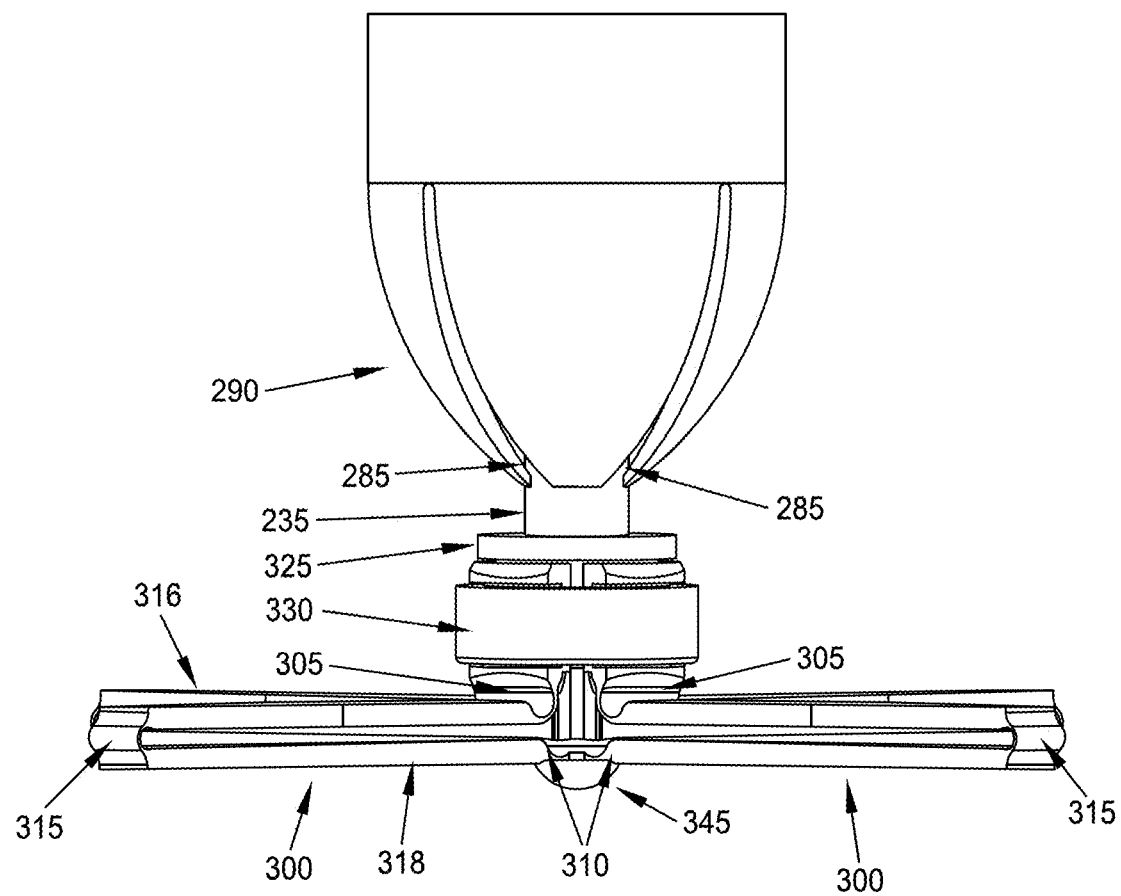
FIGS. 24-26 are schematic views showing still further aspects of the surgical mesh delivery device of FIG. 19.
Figure 25:
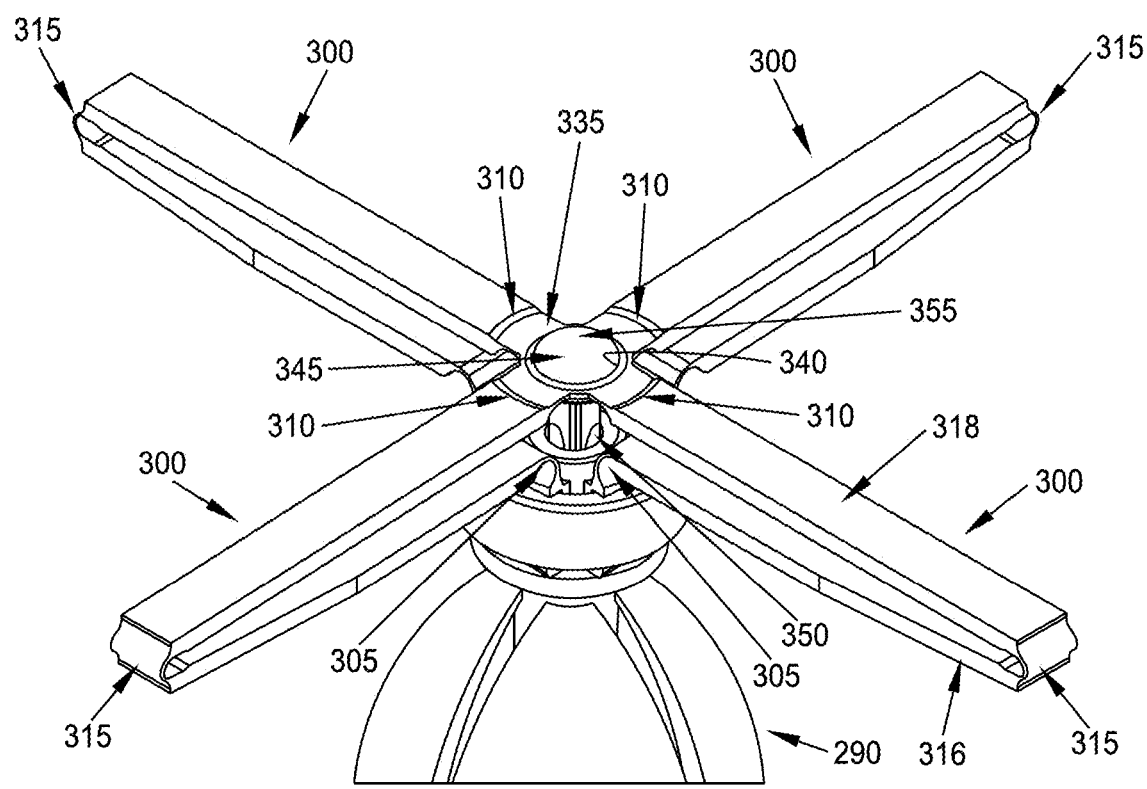
Figure 26:
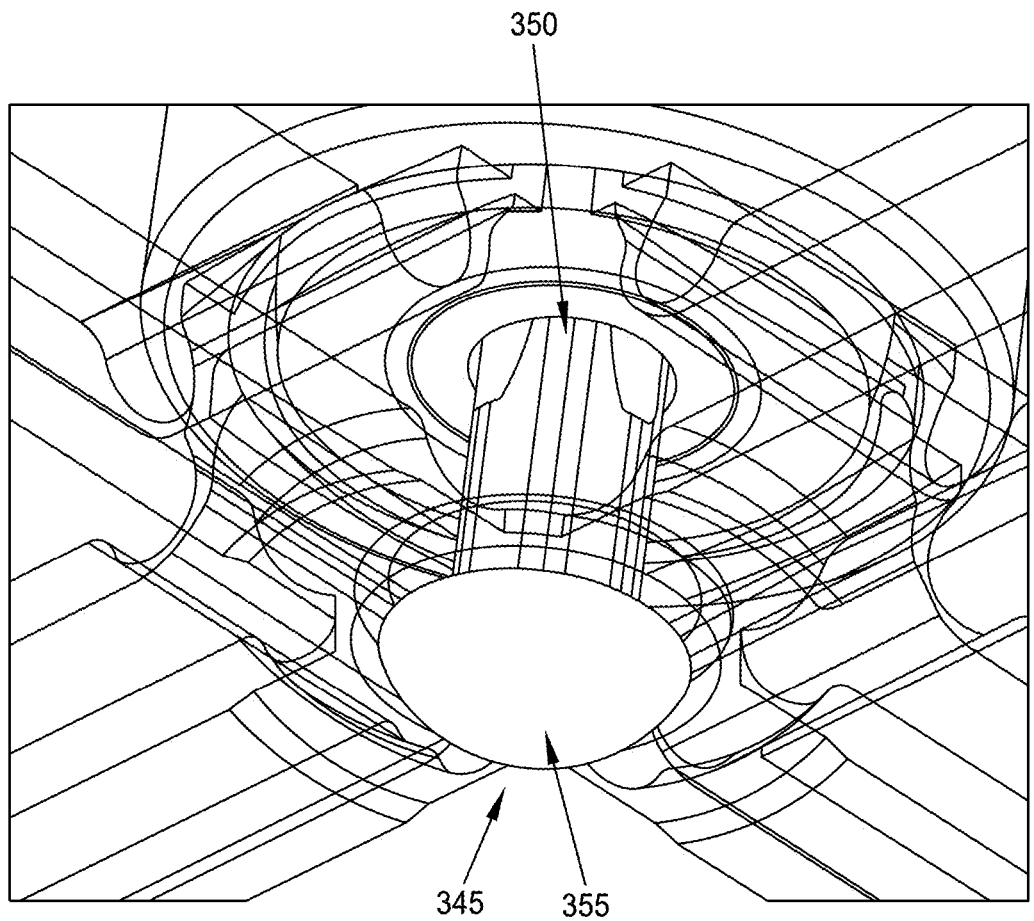

Looking now at FIG. 21, distal housing 225 generally comprises a proximal mount 270 fixedly mounted to distal end 215 of hollow outer tube 210, and an atraumatic distal shroud 275 enclosing a hollow cavity 280. Distal shroud 275 is preferably formed out of an elastic material (e.g., silicone), and comprises at least one distal slot 285 formed in a cone-shaped distal tip 290 for permitting an element carrying a surgical mesh thereon and contained within hollow cavity 280 to be selectively projected out of (or back into) hollow cavity 280, as will hereinafter be discussed in further detail.

In one preferred form of the invention, distal tip 290 comprises four flexible leaflets (not shown) created by the at least one distal slot 285 formed in cone-shaped distal tip 290.

It should be appreciated that the dimensions and/or shape of distal housing 225 may vary depending on the size of surgical mesh to be used with device 205, and the lengths of hollow outer tube 210, hollow inner tube 235 and central rod 250 can be varied depending on the surgical procedure to be performed and/or the size of a patient (i.e., a larger distal housing 225 for holding a larger surgical mesh, and/or longer tubes/rods for patients with larger abdomens).

It should also be appreciated that due to the atraumatic nature of distal shroud 275 of distal housing 225, device 205 can be used to facilitate blunt dissection between tissue planes during minimally invasive procedures and during open surgical interventions of the abdomen, groin or other soft tissue targets.

Looking now at FIGS. 20-26, there is shown a surgical mesh carriage 295 formed in accordance with the present invention. Carriage 295 is configured to be contained within hollow cavity 280 of distal housing 225 in its folded configuration (discussed in further detail below) and comprises a plurality of legs 300, with each of the plurality of legs 300 comprising a first hinged end 305 configured to mount to distal end 240 of hollow inner tube 235, a second hinged end 310 configured to mount to distal end 255 of central rod 250, and a flexible connection 315 disposed between first hinged end 305 and second hinged end 310. See FIGS. 24 and 25. In one form of the present invention, the plurality of legs 300 may comprise eight legs. In another form of the present invention, the plurality of legs 300 may comprise three legs, four legs, etc.

When the plurality of legs 300 are contained within hollow cavity 280 of distal housing 225, the plurality of legs 300 are each in their radially-reduced/folded configuration (see FIG. 21), with each of the plurality of legs 300 assuming a position in which legs 300 are disposed generally parallel to the longitudinal axis of hollow outer tube 210. When the plurality of legs 300 are fully projected out of hollow cavity 280 of distal housing 225 (discussed in further detail below), the plurality of legs 300 assume their radially-expanded/unfolded configuration (see FIG. 25), with each of the plurality of legs 300 hinging on each of their respective first hinged ends 305, whereby to assume a position in which legs 300 are disposed generally perpendicular to the longitudinal axis of hollow outer tube 210. In this way, carriage 295 functions in a manner similar to an umbrella, wherein movement of a central rod hinges a plurality of legs to expand the plurality of legs, however, with the present invention, plurality of legs 300 have increased durability due to the presence of flexible connection 315 disposed between first hinged end 305 and second hinged end 310 of each leg 300.

Legs 300 are preferably formed out of a rigid material, but may alternatively be formed out of a flexible or resilient material. In one preferred form of the invention, legs 300 are formed out of polypropylene.

In one preferred form of the invention, each of the plurality of legs 300 comprises a first portion 316 and a second portion 318. First portion 316 is disposed between first hinged end 305 and flexible connection 315 and second portion 318 is disposed between flexible connection 315 and second hinged end 310. First portion 316 is disposed parallel with second portion 318 (see FIGS. 24 and 25). It should be appreciated that in both the radially-reduced configuration and the radially-expanded configuration of plurality of legs 300, first portions 316 and second portions 318 of each of the plurality of legs 300 remain in parallel disposition with one another.

In one preferred form of the present invention, first hinged ends 305 of each of the plurality of legs 300 are received in seats 320 formed in a collar 325 which is, in turn, mounted to distal end 240 of hollow inner tube 235. A circumferentially-extending locking ring 330 is preferably mounted over first hinged ends 305 seated in their respective seats 320 formed in collar 325 in order to fixedly mount first hinged ends 305 of legs 300 to collar 325 (and hence, to distal end 240 of hollow inner tube 235).

Second hinged ends 310 of each of the plurality of legs 300 are mounted to distal end 255 of central rod 250 in a manner that will be apparent to one of skill in the art in view of the present disclosure. In a preferred form of the invention, second hinged ends 310 of each of the plurality of legs 300 are formed integral with each other so as to form a base 335 having a central opening 340 formed therein. See FIG. 25. Base 335 is mounted to distal end 255 of central rod 250 via a plug 345 having a proximal end 350 that is fixedly mounted to distal end 255 of central rod 250, and a distal end 355 having a diameter wider than the diameter of central opening 340. Plug 345 is passed through central opening 340 of base 335 such that proximal end 350 of plug 345 is mounted to distal end 255 of central rod 250, and such that distal end 355 of plug 345 is disposed distal to base 335, whereby to provide a bearing for moving second hinged ends 310 of each of the plurality of legs 300 in concert longitudinally distally or proximally as central rod 250 is moved distally or proximally, as will hereinafter be discussed in further detail.

As a result of the foregoing construction, it will be appreciated that it is possible to (i) selectively advance carriage 295 distally (or proximally) by advancing hollow inner tube 235 distally (or proximally) relative to hollow outer tube 210, (ii) selectively move the plurality of legs 300 such that the plurality of legs 300 assume a radially-expanded configuration wherein each of the plurality of legs hinges on each of their respective first hinged ends 305 (whereby to assume a position in which legs 300 are disposed generally perpendicular to the longitudinal axis of hollow outer tube 210) by advancing central rod 250 distally relative to hollow outer tube 210, and (iii) selectively move the plurality of legs 300 such that the plurality of legs 300 assume a radially-reduced configuration wherein each of the plurality of legs hinges on each of their respective first hinged ends 305 (whereby to assume a position in which legs 300 are disposed generally parallel to the longitudinal axis of hollow outer tube 210) by advancing central rod 250 proximally relative to hollow outer tube 210, as will hereinafter be discussed in further detail.

Figure 27:
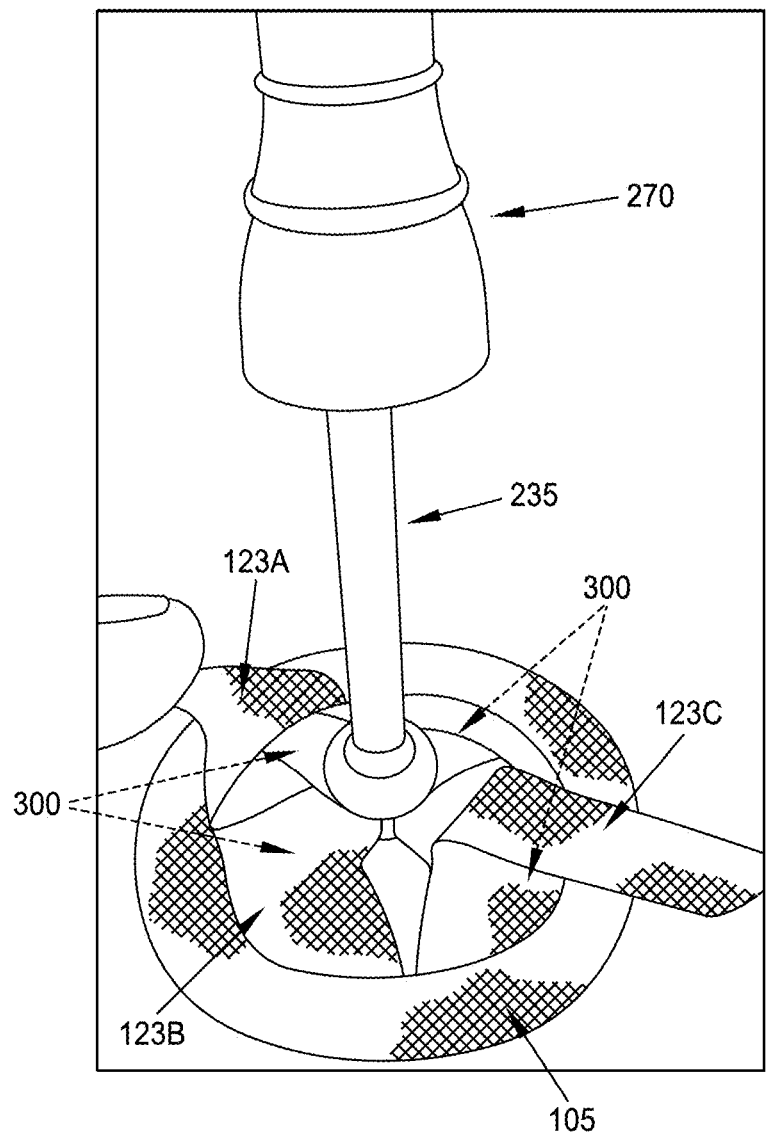
FIGS. 27 and 28 are schematic views showing surgical mesh being attached to the surgical mesh delivery device of FIG. 19.
Figure 28:
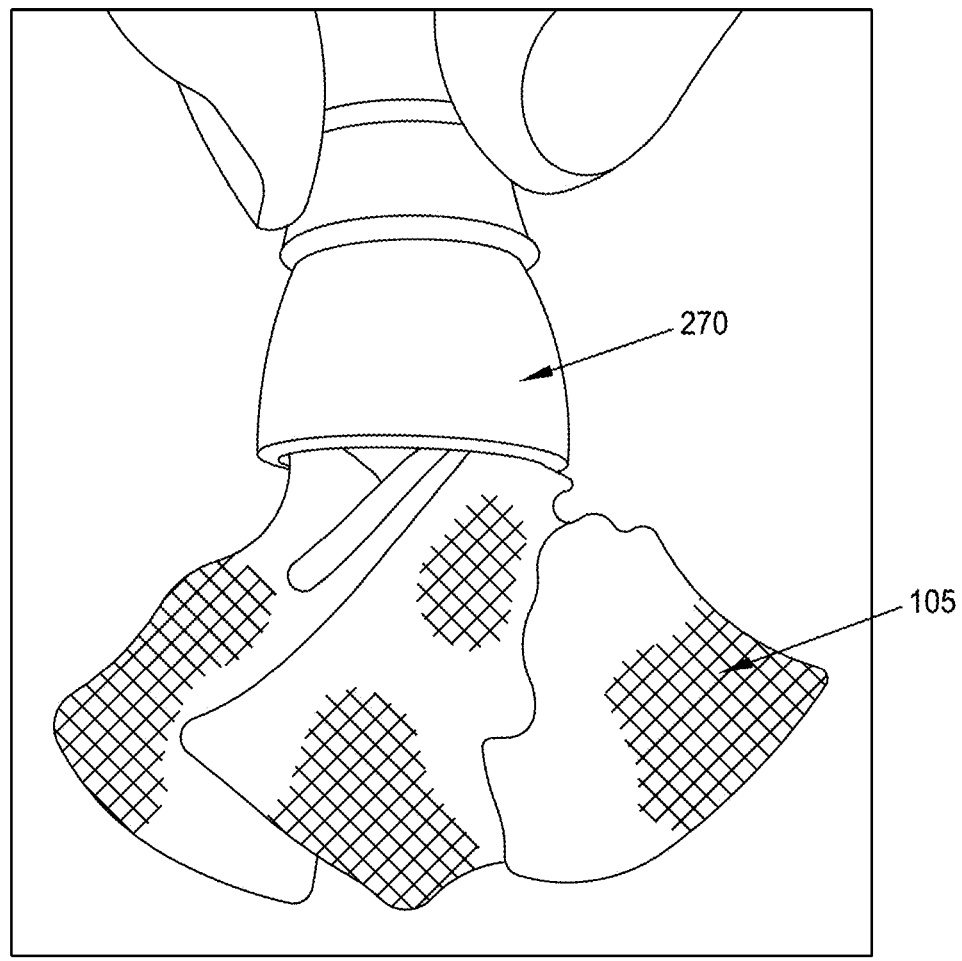
Figure 29:
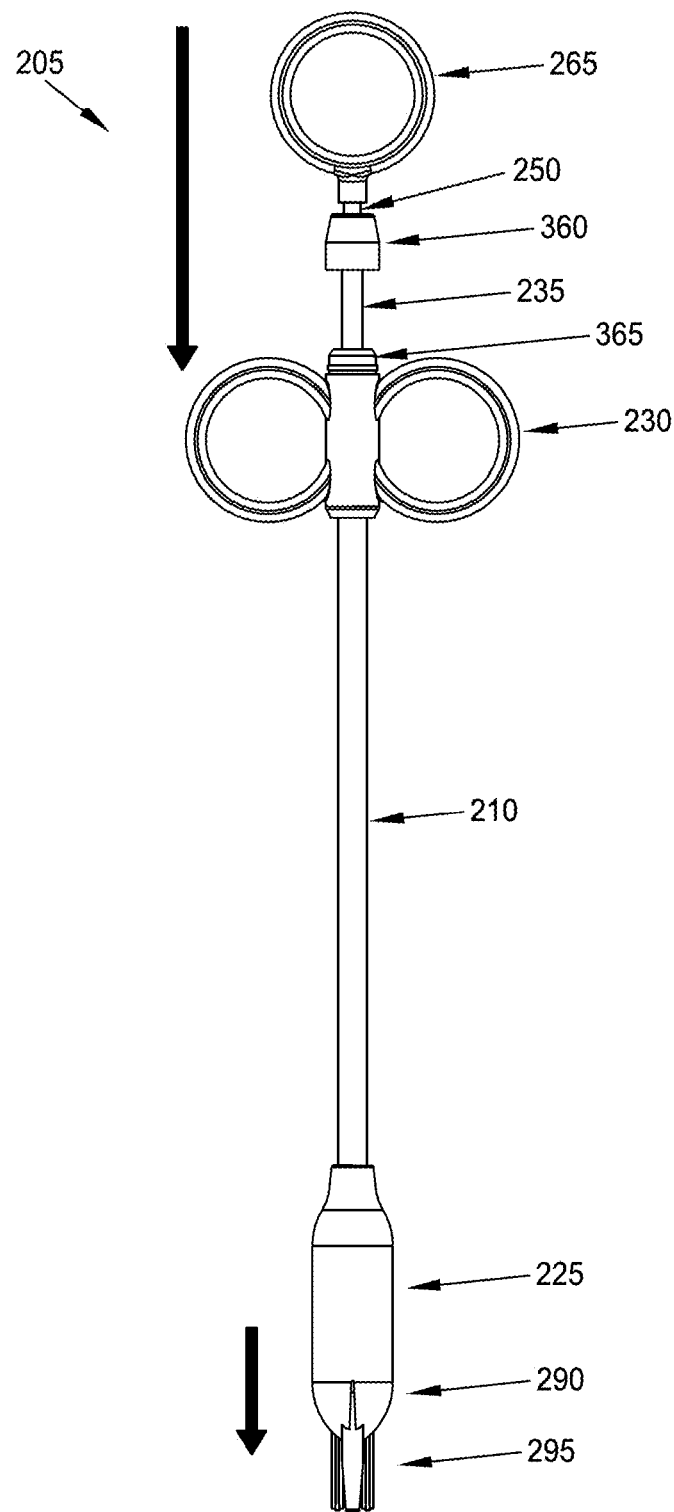
FIGS. 29-38 are schematic views showing operation of the surgical mesh delivery device of FIG. 19.
Figure 30:
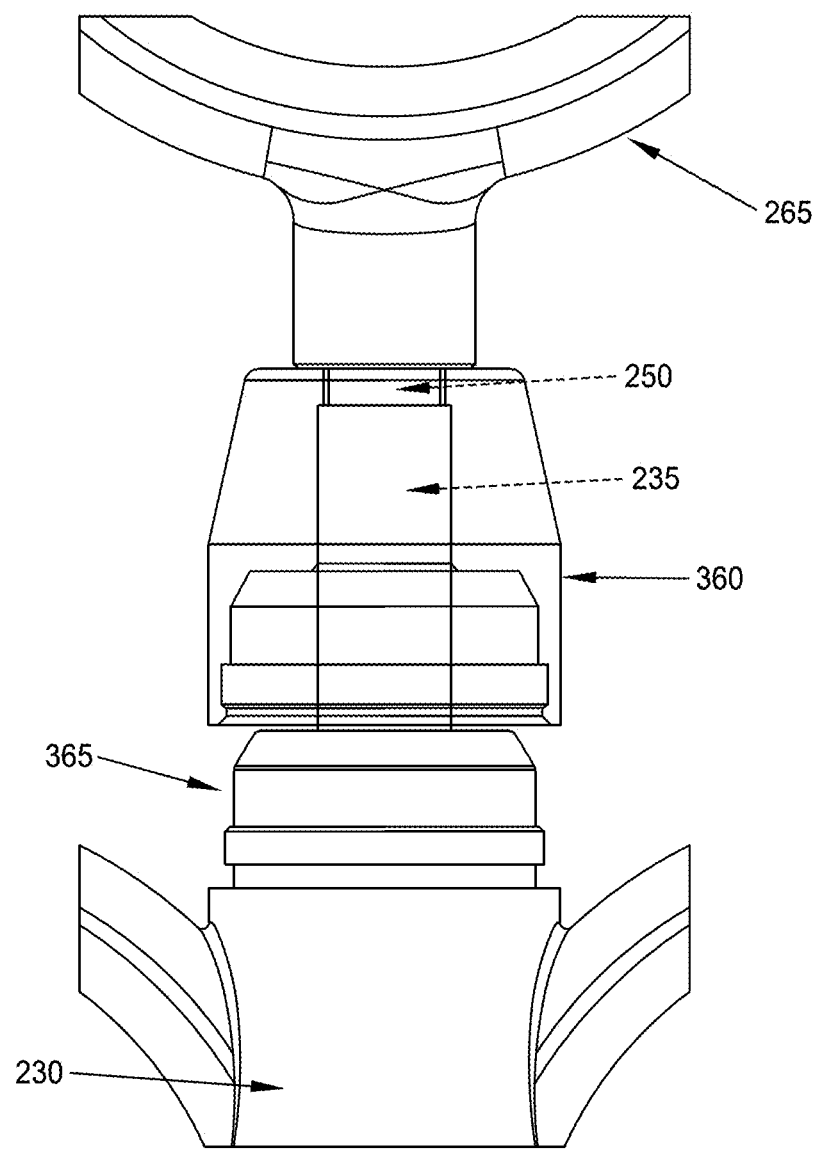
Figure 31:
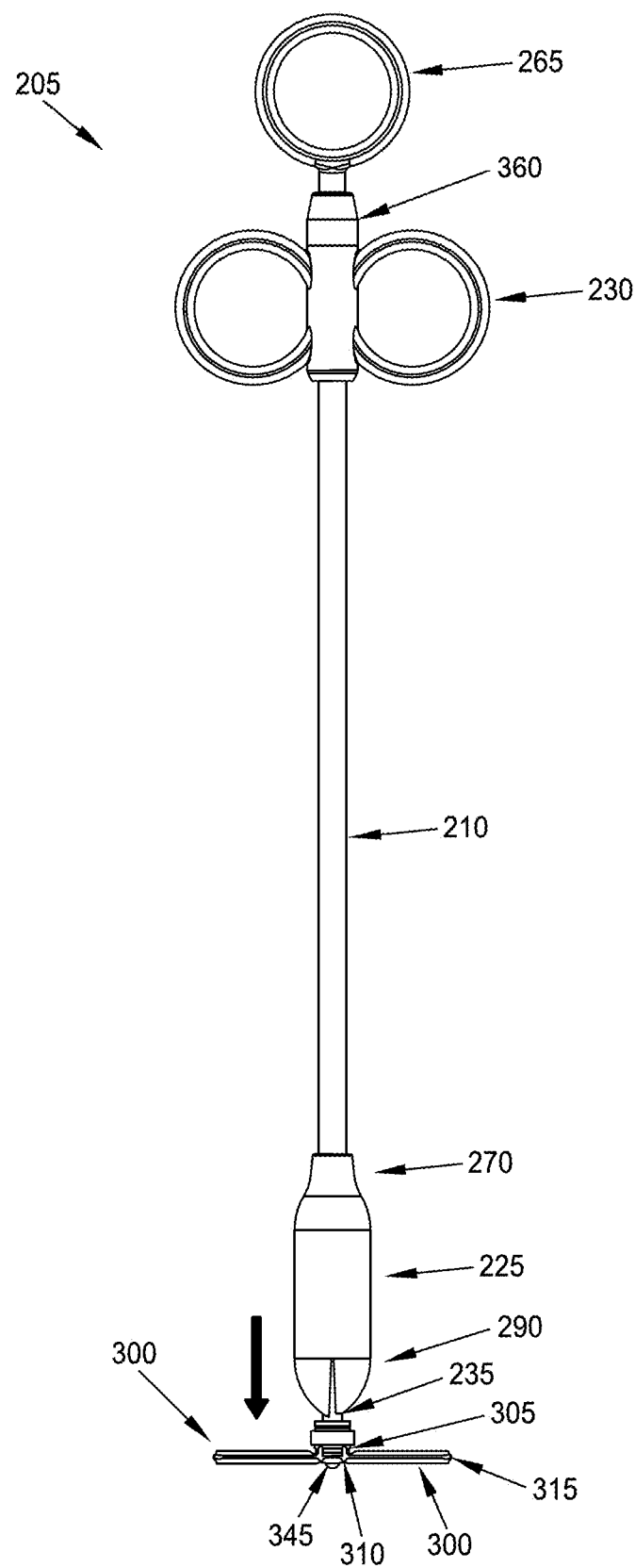
Figure 32:
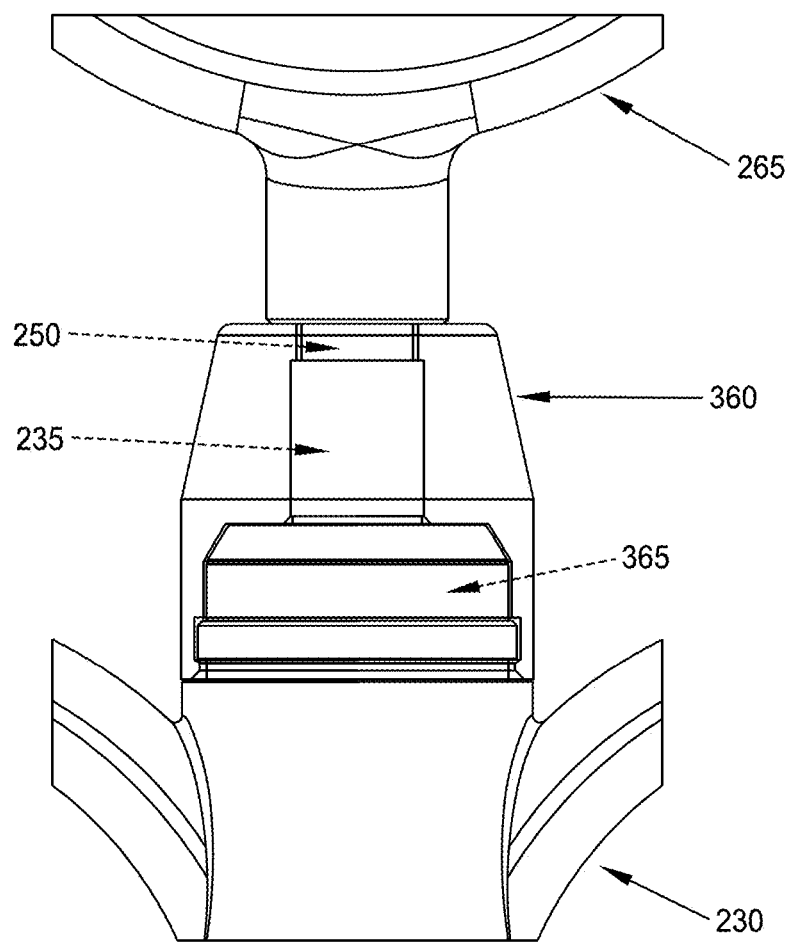

Looking now at FIGS. 27 and 28, a surgical mesh (e.g., the aforementioned segmented skirted surgical mesh 105 or other surgical mesh) may be attached to legs 300 such that the surgical mesh may be advanced to a surgical site while legs 300 (and hence, the surgical mesh attached thereto) are in a radially-reduced configuration and protected by distal shroud 275 (not shown in FIGS. 27 and 28), and thereafter expanded at the surgical site so as to assume a generally planar, radially-expanded configuration held in position by legs 300.

More particularly, in one preferred form of the present invention, where the aforementioned segmented skirted surgical mesh 105 is to be attached to legs 300 for advancement to, and deployment at, a surgical site using surgical mesh delivery device 205, legs 300 are disposed between base layer 110 of surgical mesh 105 and segmented continuous skirt or rim 115 while legs 300 are in their radially-expanded configuration with legs 300 extending between base layer 110 and segments or flaps 123A, 123B, 123C, etc. of the segmented continuous skirt or rim 115 (see FIG. 27). Second hinged ends 310 of legs 300 can then be moved proximally (i.e., by moving central rod 250 proximally), whereby to leave surgical mesh 105 attached to legs 300 as legs 300 are moved into their radially-reduced configuration (see FIG. 28). Thereafter (or simultaneously), carriage 295 (now having surgical mesh 105 attached thereto) may be moved proximally into cavity 280 of distal shroud 275. At this point, blunt dissector, delivery and deployment device 205 is configured to be used to deliver the surgical mesh to a surgical site.

It will be appreciated that the surgical mesh (e.g., the aforementioned segmented skirted surgical mesh 105 or other surgical mesh) may be mounted to legs 300 in the manner discussed above by the end user (e.g., a surgeon) or, if desired, device 205 may be provided with the surgical mesh already mounted and contained within distal shroud 275 ready for use.

In use, and looking now at FIGS. 29-33, a surgeon advances surgical mesh delivery device 205 having a surgical mesh (e.g., segmented skirted surgical mesh 105 or other surgical mesh) mounted to legs 300 and contained within cavity 280 of distal shroud 275 in a radially-reduced configuration to the surgical site (e.g., through a small incision, through intervening tissue and into the peritoneal space). It will be appreciated that inasmuch as the surgical mesh is in a radially-reduced (i.e., folded) configuration attached to carriage 295 and protected within shroud 275, the surgeon can advance the surgical mesh (i.e., distal housing 225) through a radially-reduced opening (e.g., a small incision) to an internal surgical site and, once distal housing 225 (or at least the distalmost portion thereof) is disposed distal to the tissue requiring repair, the surgeon can then use device 205 to cause legs 300 (and hence, the surgical mesh attached thereto) to be pushed out of distal housing 225 and assume their radially-expanded (i.e., unfolded) configuration. As a result, it is possible to minimize trauma to the patient while advancing the surgical mesh to the internal site where it is to be used. In other words, distal housing 225 allows for safe, atraumatic manipulation and dissection of tissue as device 205 is moved through a patient's body to an internal surgical site. It should also be appreciated that removable pre-deployment locking clip 267 prevents premature deployment of carriage 295 out of distal shroud 275 during advancement of device 205 to the internal surgical site.

Once the distal tip 290 of shroud 275 of distal housing 225 is immediately proximate the surgical site, the surgeon removes pre-deployment locking clip 267 and moves hollow inner tube 235 distally by moving actuation element 265 distally, whereby to project carriage 295 (i.e., plurality of legs 300 containing surgical mesh attached thereto) out of distal tip 290 of shroud 275. It will be appreciated that the at least one slot 285 and the elastic nature of shroud 275 and distal tip 290 together permit carriage 295 to be easily projected out of shroud 275 by applying light distally-directed force to hollow inner tube 235 via actuation element 265.

To this end, and in order to provide tactile and audible feedback to the surgeon (e.g., to inform the surgeon when carriage 295 is projected distally beyond distal tip 290 of distal housing 225, and to inform the surgeon when the surgical mesh is delivered to the repair site), a locking collar 360 is preferably mounted to (or formed integral with) proximal end 245 of hollow inner tube 235. Locking collar 360 is configured to mate with a counterpart locking tab 365 formed on the proximal end of handle 230. As actuation element 265 is moved distally, central rod 250 and hollow inner tube 235 are also moved distally. And as hollow inner tube 235 reaches its distalmost position, locking collar 360 engages the proximalmost surface of locking collar 360, providing a tactile indication (e.g., resistance to further distal movement of actuation element 265) to the surgeon to confirm that hollow inner tube 235 (and hence, carriage 295 mounted thereto) is disposed at its distalmost position (i.e., with carriage 295, and hence the surgical mesh carried thereon fully projected beyond distal tip 290 of shroud 275). See FIG. 30. Further distal movement of actuation element 265 causes further distal movement of central rod 250. As this occurs, (i) distal movement of central rod 250 bears against base 335 of the plurality of legs 300 (and hence, second hinged ends 310 of the plurality of legs 300) and effects flexing of each of the plurality of legs 300 at first hinged ends 305, causing the plurality of legs 300 to project radially outboard so as to be generally perpendicular to the longitudinal axis of central rod 250 (i.e., so as to assume their radially-expanded/unfolded configuration), and (ii) locking collar 360 "snaps" over locking tab 365, providing a tactile and audible indication to the surgeon that central rod 250 is disposed at its distalmost position and thus the plurality of legs 300 (and the surgical mesh carried thereon) are in their radially-expanded/unfolded configuration, and hence the surgical mesh is delivered to the site of the repair. See FIGS. 31 and 32.

Figure 33:
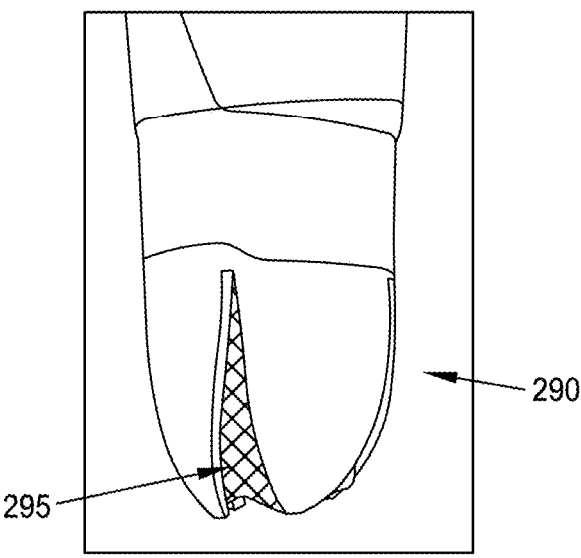
Figure 34:
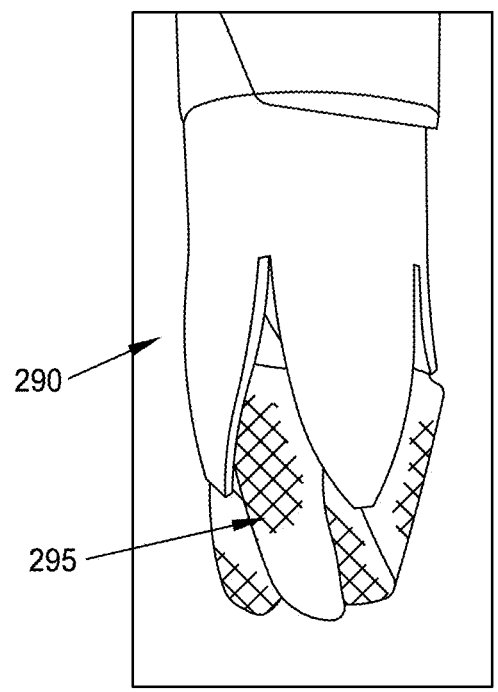
Figure 35:
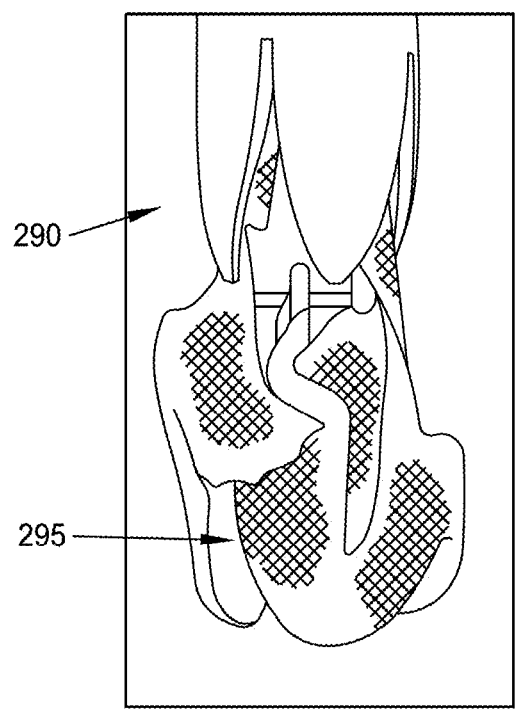
Figure 36:
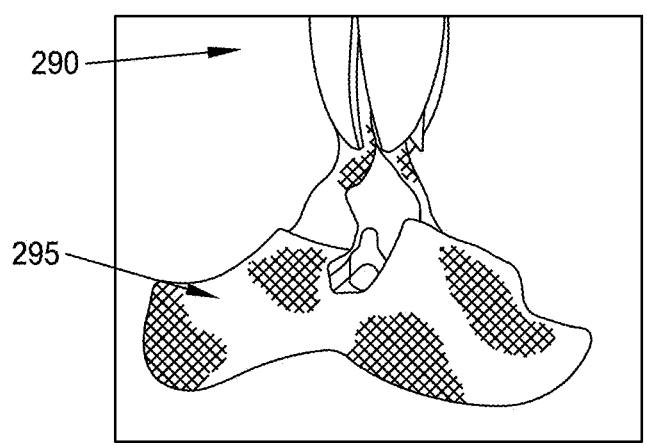
Figure 37:
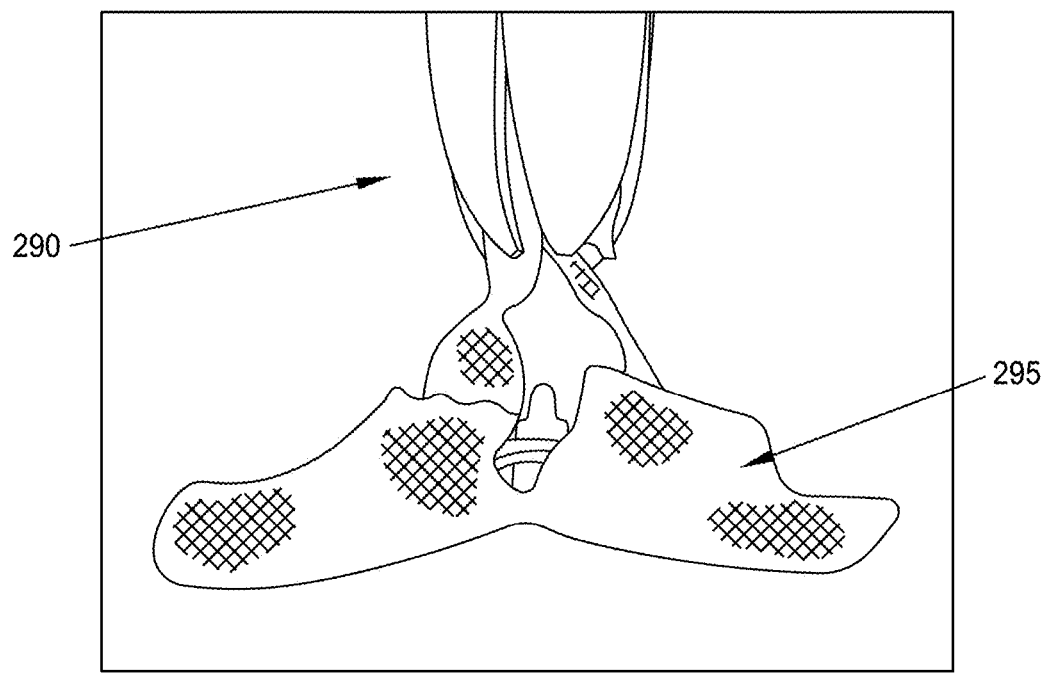

FIGS. 33-37 show carriage 295 (having a surgical mesh attached thereto) being deployed out of distal tip 290 of distal housing 225, with FIGS. 33-35 showing legs 300 disposed in their radially-reduced configuration (i.e., folded configuration), and with FIGS. 36 and 37 showing legs 300 assuming their radially-expanded configuration (i.e., their unfolded configuration).

If desired, once the surgical mesh is fully deployed out of distal tip 290 of distal housing 225, with the plurality of legs 300 (and hence, the surgical mesh carried thereon) in their radially-expanded/unfolded configuration, the surgeon may rotate device 205 (e.g., using handle 230) along its longitudinal axis so as to "spin" the surgical mesh carried on the plurality of legs 300 in order to make room for/ensure proper deployed placement of the surgical mesh at the desired site.

It will be appreciated that after the foregoing procedure has been performed, the surgical mesh carried on legs 300 (e.g., the aforementioned novel segmented skirted surgical mesh 105) may be used to effect a surgical repair (e.g., of a hernia) in a manner that will be apparent to one of skill in the art in view of the present disclosure. However, it should be appreciated that use of blunt dissector, delivery and deployment device 205 to deliver surgical mesh to an internal repair site does not require that the surgical mesh ultimately be sutured (or otherwise secured) to surrounding tissue. Once the surgical mesh has been utilized for the desired surgical repair, device 205 may be removed from the surgical site.

Figure 38:
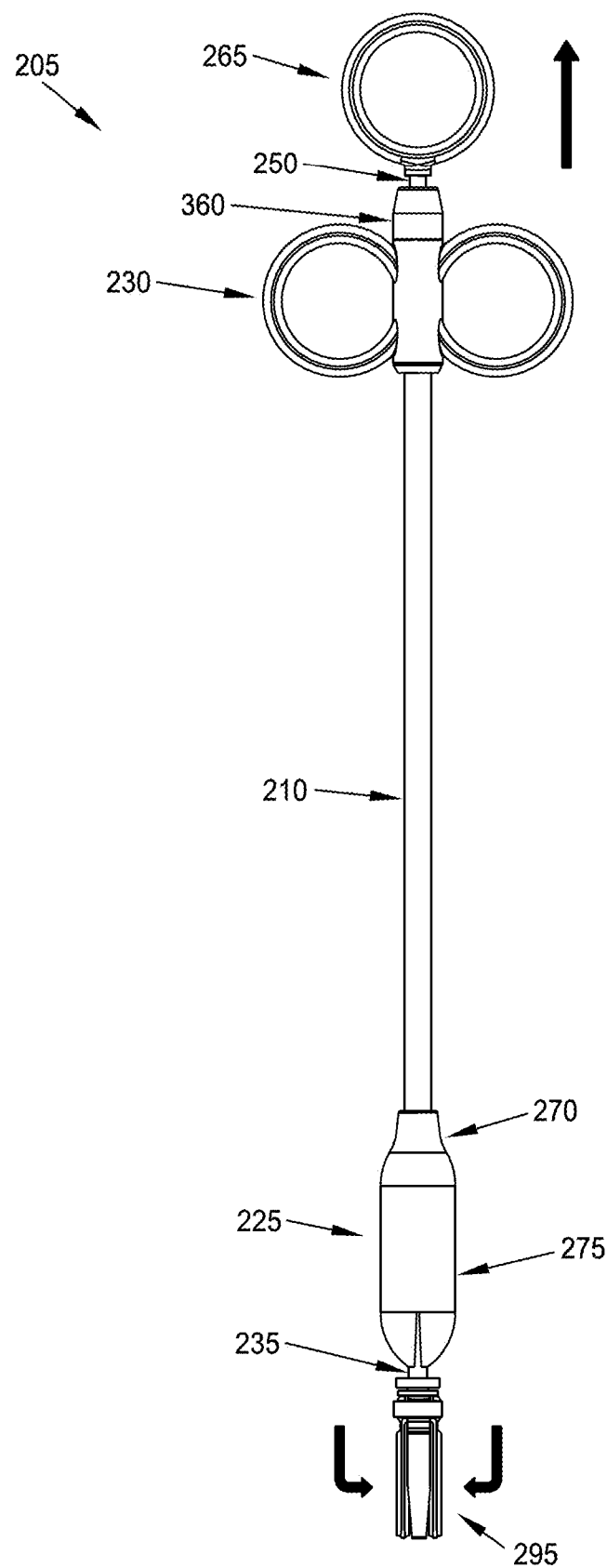

To that end, and looking now at FIG. 38, the surgeon may move actuation element 265 proximally, whereby to move central rod 250 proximally. As this occurs, base 335 of the plurality of legs 300 is moved proximally, causing each of the plurality of legs 300 to flex at first hinged end 305, such that each of the plurality of legs 300 are disposed generally parallel to the longitudinal axis of central rod 250 (i.e., such that legs 300 are in their radially-reduced/folded configuration). Further proximal movement of actuation element 265 may be applied in order to move hollow inner tube 235 proximally, whereby to draw carriage 295 into distal shroud 275 such that carriage 295 is again shrouded, and thereafter surgical mesh delivery device 205 can be withdrawn proximally from the surgical site (e.g., through an incision).

However, it should be appreciated that, due to the flexible nature of the plurality of legs 300, once the surgical mesh has been utilized for the desired surgical repair, a surgeon may simply pull out device 205 without withdrawing legs 300 back into distal housing 225, if desired.

Thus, use of all-in-one blunt dissector, delivery and deployment device 205 allows for fast and simple tissue repair with minimal trauma to a patient.

Use of Blunt Dissector, Delivery and Deployment Device 205 with Coated Surgical Mesh In practice, it has been found that it is often desirable to configure a surgical mesh so that it will encourage tissue ingrowth into one side of the surgical mesh (e.g., the abdominal wall side of the surgical mesh) while preventing tissue ingrowth into the opposite side of the surgical mesh (e.g., the abdominal cavity side of the surgical mesh). To this end, it is common to apply an ingrowth-preventing coating formed out of a permanent or resorbable non-porous flexible material (e.g., an elastomer such as silicone or urethane or a flexible resorbable material) to one side of the surgical mesh so that the ingrowth-preventing coating closes off the pores of the mesh (e.g., in the case of a knitted/woven mesh, the pores of the knitted/woven material forming the mesh, and in the case of a non-knitted/non-woven mesh, the pores between the polypropylene fibers, and also the recesses of the non-knitted/non-woven material forming the mesh). It should be appreciated that device 205 may also be used with coated surgical mesh.

When device 205 is to be used with a silicone coated surgical mesh, a resin may be added to the silicone coating of the surgical mesh so that the silicone coating of the surgical mesh does not interfere with any silicone present in device 205 (e.g., distal shroud 275).

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:
1. Apparatus for delivering a surgical mesh, the apparatus comprising:
    a hollow outer tube having a distal end and a proximal end;
    a distal housing mounted to the distal end of the hollow outer tube;
    a hollow inner tube having a distal end and a proximal end, wherein the hollow inner tube is slidably disposed within the hollow outer tube;
    a central rod having a distal end and a proximal end, wherein the central rod is slidably disposed within the hollow inner tube;
    an actuation element mounted to the proximal end of the central rod; and
    a surgical mesh carriage comprising a plurality of legs, wherein each of the plurality of legs comprises a first hinged end mounted to the distal end of the hollow inner tube and a second hinged end mounted to the distal end of the central rod;
    wherein the distal housing comprises a proximal mount fixedly mounted to the distal end of the hollow outer tube and an atraumatic distal shroud comprising a cone-shaped tip having at least one expandable slot.
2. The apparatus according to claim 1 wherein the apparatus is configured such that when (i) the actuation element is moved distally to a first location, the central rod and the hollow inner tube move distally so as to move the surgical mesh carriage out of the distal housing, and (ii) the actuation element is moved distally to a second location the central rod moves distally and hinges each of the plurality of legs at their respective first hinged ends so that the plurality of legs assume a radially-expanded configuration.
3. The apparatus according to claim 2 wherein tactile feedback is provided to a user when the actuation element reaches the first location.

4. The apparatus according to claim 2 wherein audible feedback is provided to a user when the actuation element reaches the second location.

5. The apparatus according to claim 2 wherein when the plurality of legs are in the radially-expanded configuration, the plurality of legs are disposed generally perpendicular to the longitudinal axis of the hollow outer tube.

6. The apparatus according to claim 2 further comprising a handle mounted to the proximal end of the hollow outer tube.

7. The apparatus according to claim 6 wherein the proximal end of the hollow inner tube comprises a locking collar and the handle comprises a locking tab, and further wherein the locking collar is configured to mate with the locking tab.

8. The apparatus according to claim 7 wherein the locking collar snaps over the locking tab so as to provide audible feedback to a user indicating that the plurality of legs are in the radially-expanded configuration.

9. The apparatus according to claim 1 wherein each of the plurality of legs further comprises a flexible connection disposed between the first hinged end and the second hinged end.

10. The apparatus according to claim 9 wherein each of the plurality of legs comprises a first portion disposed between the first hinged end and the flexible connection, and a second portion disposed between the flexible connection and the second hinged end, and further wherein the first portion is disposed parallel with the second portion.

11. The apparatus according to claim 1 wherein the second hinged ends of the plurality of legs are formed integral with each other so as to form a base having a central opening mounted to the distal end of the central rod.

12. The apparatus according to claim 11 wherein the distal end of the central rod comprises a plug with a distal portion having a diameter wider than the diameter of the central opening.

13. The apparatus according to claim 1 wherein the atraumatic distal shroud is formed out of an elastic material.

14. The apparatus according to claim 13 wherein the elastic material comprises silicone.

15. The apparatus according to claim 1 wherein the cone-shaped tip comprises four flexible leaflets formed by the at least one slot.

16. The apparatus according to claim 1 wherein the distal end of the hollow inner tube comprises a collar and further wherein the first hinged ends of each of the plurality of legs are received in a plurality of seats formed in the collar.

17. The apparatus according to claim 16 wherein a locking ring is mounted over the first hinged ends of the plurality of legs in the plurality of seats formed in the collar.

18. A method for delivering a surgical mesh, the method comprising:
  providing apparatus for delivering a surgical mesh, the apparatus comprising:
    a hollow outer tube having a distal end and a proximal end;
    a distal housing mounted to the distal end of the hollow outer tube;
    a hollow inner tube having a distal end and a proximal end, wherein the hollow inner tube is slidably disposed within the hollow outer tube;
    a central rod having a distal end and a proximal end, wherein the central rod is slidably disposed within the hollow inner tube;
    an actuation element mounted to the proximal end of the central rod; and
    a surgical mesh carriage comprising a plurality of legs, wherein each of the plurality of legs comprises a first hinged end mounted to the distal end of the hollow inner tube and a second hinged end mounted to the distal end of the central rod;
    wherein the distal housing comprises a proximal mount fixedly mounted to the distal end of the hollow outer tube and an atraumatic distal shroud comprising a cone-shaped tip having at least one expandable slot;
  advancing the apparatus through an incision to a surgical site;
  moving the actuation element distally to a first location, whereby to project the surgical mesh carriage out of the distal housing;
  moving the actuation element distally to a second location, whereby to hinge each of the plurality of legs at their respective first hinged ends and cause the plurality of legs to assume a radially-expanded configuration; and
  delivering a surgical mesh to the surgical site.

19. Apparatus for delivering a surgical mesh, the apparatus comprising:
  a hollow outer tube having a distal end and a proximal end;
  a distal housing mounted to the distal end of the hollow outer tube;
  a hollow inner tube slidably disposed within the hollow outer tube having a distal end and a proximal end, wherein the proximal end of the hollow inner tube comprises a locking collar;
  a central rod having a distal end and a proximal end, wherein the central rod is slidably disposed within the hollow inner tube;
  an actuation element mounted to the proximal end of the central rod;
  a surgical mesh carriage comprising a plurality of legs, wherein each of the plurality of legs comprises a first hinged end mounted to the distal end of the hollow inner tube and a second hinged end mounted to the distal end of the central rod; and
  a handle comprising a locking tab mounted to the proximal end of the hollow outer tube;
  wherein the distal housing comprises a proximal mount fixedly mounted to the distal end of the hollow outer tube and an atraumatic distal shroud comprising a cone-shaped tip having at least one expandable slot;
  wherein the apparatus is configured such that when (i) the actuation element is moved distally to a first location, the central rod and the hollow inner tube move distally so as to move the surgical mesh carriage out of the distal housing, and (ii) the actuation element is moved distally to a second location the central rod moves distally and hinges each of the plurality of legs at their respective first hinged ends so as to assume a radially-expanded configuration; and
  wherein distal movement of the actuation element to the second location causes the locking collar to audibly snap over the locking tab so as to provide feedback to a user indicating that the plurality of legs are in the radially-expanded configuration.

* * * * *